United States Patent [19]

Ohtani et al.

[11] Patent Number: 5,597,943
[45] Date of Patent: Jan. 28, 1997

[54] PHOSPHOLIPASE $A_2$ INHIBITOR

[75] Inventors: Mitsuaki Ohtani, Nara; Shigeru Matsutani, Hashimoto; Tadashi Yoshida, Toyono-gun; Kazushige Tanaka, Amagasaki; Yasuhiko Fujii, Kobe; Kazuhiro Shirahase, Neyagawa, all of Japan

[73] Assignee: Shionogi & Co., Ltd., Osaka, Japan

[21] Appl. No.: 571,698

[22] Filed: Dec. 13, 1995

Related U.S. Application Data

[63] Continuation of Ser. No. 267,002, Jun. 21, 1994, abandoned, which is a continuation of Ser. No. 983,856, filed as PCT/JP92/00802, Nov. 19 1992, published as WO93/01157 Jan. 21, 1993, abandoned.

[30] Foreign Application Priority Data

Jul. 3, 1991 [JP] Japan ................................ 3-162847

[51] Int. Cl.⁶ .................................................. C07C 69/76
[52] U.S. Cl. ............................ 560/42; 549/393; 549/305; 560/11; 560/18; 560/57; 560/64; 560/65; 560/72; 560/73; 560/84; 560/85; 560/86
[58] Field of Search .................................. 549/393, 305; 560/42, 11, 18, 57, 64, 65, 72, 73, 84, 85, 86

[56] References Cited

U.S. PATENT DOCUMENTS 3,859,307 1/1975 Carr et al. .............................. 549/393

OTHER PUBLICATIONS

Yoshida et al., The Journal of Antibiotics, vol. 44, No. 12, Dec., 1991, pp. 1467–1470.
Yoshida et al., Chemical Abstracts, vol. 117, No. 17, 26 Oct., 1992 Abstract No. 169572h JP-A-4 159 251.
Yoshida et al., Chemical Abstracts, vol. 117, No. 21, 23 Nov., 1992 Abstract No. 210731x JP-A-4 117 346.

*Primary Examiner*—Nicky Chan
*Attorney, Agent, or Firm*—Wenderoth, Lind & Ponack

[57] ABSTRACT

The present invention relates to the new thielocin derivatives, which exhibit phospholipase $A_2$ inhibitory activity of the formula:

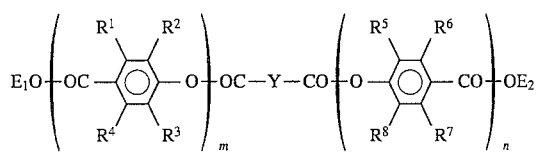

wherein $R^1$, $R^2$, $R^3$, $R^4$, $R^5$, $R^6$, $R^7$, and $R^8$ are independently hydrogen, lower alkyl, lower alkoxy, hydroxy, or halogen;

$E_1$ and $E_2$ are independently hydrogen, or an ester residue;

m and n are independently an integer of 0 to 4;

—Y— is a bivalent group which is selected from the group consisiting of the following radicals:

$-CH_2CH_2-$, $-CH=CH-$,

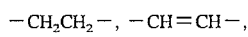

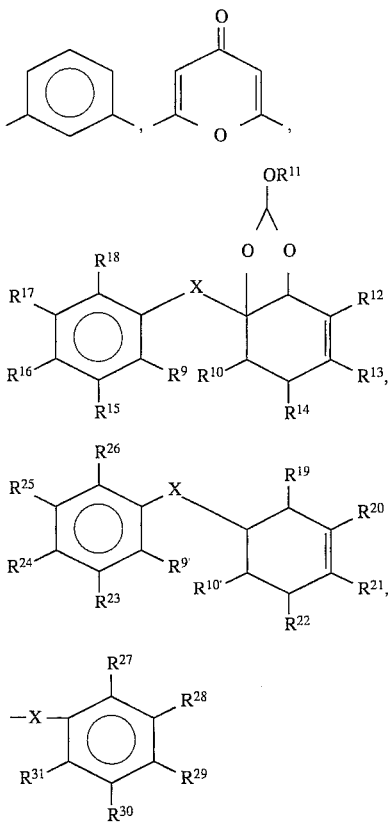

or

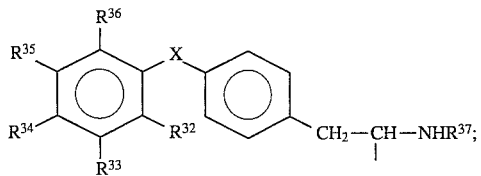

or the salts thereof.

4 Claims, No Drawings

PHOSPHOLIPASE A₂ INHIBITOR

This application is a continuation of now abandoned application Ser. No. 08/267,002, filed Jun. 21, 1994, which is a continuation of now abandoned application Ser. No. 07/983,856, filed as PCT/JP92/00802 Nov. 19, 1992 published as WO93/01157 Jan. 21, 1993.

FIELD OF THE INVENTION

The present invention relates to novel phospholipase $A_2$ inhibitors. In more particular, the present invention relates to novel compounds exhibiting an inhibiting effect on phospholipase $A_2$, which compounds are analogs of physiologically active substances, thielocins which are produced by microorganisms such as *Thielavia terricola* RF-143 belonging to Thielavia genus.

THE PRIOR ART

Phospholipase $A_2$ is an enzyme which exists in a cell and a secretory liquid, in particular, the venom of snakes, pancreas of a mammalian, blood platlets of various animals, arthritis exudate of higher animals, and so on. The enzyme specifically hydrolyzes phospholipids. For example, the enzyme specifically hydrolyzes C-2 fatty acid esters of 1,2-diacylglycerol phospholipids to form lysoglycerophospholipids and fatty acids. Phospholipid $A_2$ exhibits toxicity on nerve, muscle and heart, and anticoagulant actions in association with the above enzymatic action, and it is generally said that the enzyme may induce convulsant, hypotonia, haemolysis, edema, and so on. Further, the enzyme can also be responsible for other clinical symptoms including inflammations. It should be noted that phospholipase $A_2$ is recognized to be one of the phlogogenic substances in humans.

If the enzymatic activity of phospholipase $A_2$, which is a phlogogenic substance can be inhibited, various diseases caused by or associated with the enzymatic activity can probably be treated. Based on such assumption, substances such as mepacrine and p-bromophenacyl bromide have already been developed, and the applicants have also claimed and disclosed novel phospholipase $A_2$ inhibitors in Japanese Patent Publication (kokai) No. 286088/1990 and Japanese Patent Application No. 234955/1990. However, it is desirable to develop additional phospholipase $A_2$ inhibitors, because types of the phospholipase $A_2$ molecules are varied and the activity of one of the molecules is not the same as the other due to the difference of the structure of the molecules.

DESCRIPTION OF THE PRESENT INVENTION

The applicants have filed Japanese patent applications which claim and disclose thielocin $A_1\alpha$, $A_1\beta$, and so on, which are produced by *Thielavia terricola* RF-143 (Japanese Patent Application No. 109939/1989, etc.). Now, the applicants have chemically symthesized new various thielocin derivatives useful as medicine, and established the present invention.

Specifically, the present invention relates to thielocin derivatives of the formula:

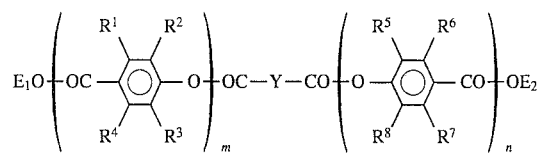

wherein
$R^1$, $R^2$, $R^3$, $R^4$, $R^5$, $R^6$, $R^7$, and $R^8$ are independently hydrogen, lower alkyl, lower alkoxy, hydroxy, or halogen;

$E_1$ and $E_2$ are independently hydrogen, or an ester residue;

m and n are independently an integer of 0 to 4;

—Y— is a bivalent group which is selected from the group consisiting of the following radicals:

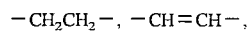

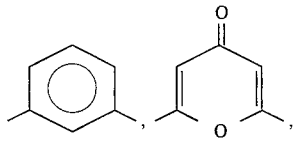

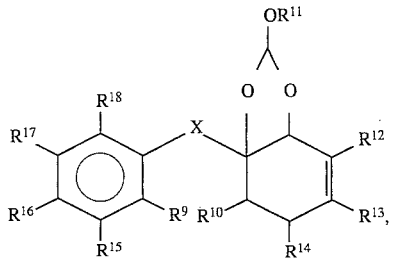

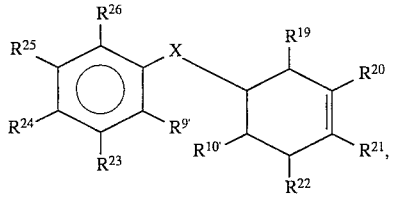

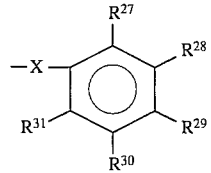

or

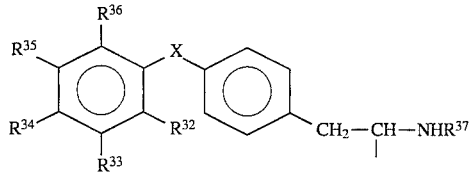

wherein
X is a single bond, $CH_2$, O, S, SO, or $SO_2$;

$R^9$ and $R^{10}$ are independently a single bond, hydrogen, lower alkyl, lower alkoxy, hydroxy, or halogen, or $R^9$ and $R^{10}$ may be combined together to form methylene, ether, sulfide, sulfinyl, or sulfone;

$R^{9'}$ and $R^{10'}$ are independently a single bond, hydrogen, lower alkyl, lower alkoxy, hydroxy, or halogen, or $R^{9'}$ and $R^{10'}$ may be combined together to form methylene, ether, sulfide, sulfinyl, or sulfone;

$R^{11}$ is hydrogen or lower alkyl;

$R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, and $R^{31}$ are independently a single bond, hydrogen, lower alkyl, lower alkoxy, hydroxy, or halogen, provided that one of $R^{9}$, $R^{15}$, $R^{16}$, $R^{17}$ and $R^{18}$, one of $R^{10}$, $R^{12}$, $R^{13}$ and $R^{14}$, one of $R^{9'}$, $R^{23}$, $R^{24}$, $R^{25}$ and $R^{26}$, one of $R^{10'}$, $R^{19}$, $R^{20}$, $R^{21}$ and $R^{22}$, and one of $R^{27}$, $R^{28}$, $R^{29}$, $R^{30}$ and $R^{31}$ are a single bond;

$R^{32}$, $R^{33}$, $R^{34}$, $R^{35}$, and $R^{36}$ are independently hydrogen, lower alkyl, lower alkoxy, hydroxy, halogen, or Z, and $R^{37}$ is hydrogen or an amino-protecting group, wherein Z is a single bond or a bivalent group of the formula:

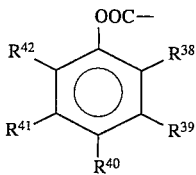

$R^{38}$, $R^{39}$, $R^{40}$, $R^{41}$, and $R^{42}$ are independently a single bond, hydrogen, lower alkyl, lower alkoxy, hydroxy, or halogen, provided that one of $R^{32}$, $R^{33}$, $R^{34}$, $R^{35}$ and $R^{36}$ is always Z, and when Z is not a single bond, one of $R^{38}$, $R^{39}$, $R^{40}$, $R^{41}$ and $R^{42}$ is a single bond or when two or more of $R^{32}$, $R^{33}$, $R^{34}$, $R^{35}$ and $R^{36}$ are Z, only one of Zs and $R^{38}$, $R^{39}$, $R^{40}$, $R^{41}$ and $R^{42}$ is a single bond;

or the salts thereof.

Several terms used in the present specification are defined below:

The term "lower alkyl" refers to $C_1$–$C_6$ alkyl such as methyl, ethyl, propyl, isopropyl, butyl, isobutyl, tert-butyl, pentyl, hexyl.

The term "lower alkoxy" refers to $C_1$–$C_6$ alkoxy such as methoxy, ethoxy, propoxy, isopropoxy, butoxy, isobutoxy, tert-butoxy, pentoxy, hexyloxy.

The term "halogen" refers to chlorine, bromine, iodine, or fluorine.

The term "ester residue" refers to an alkyl having 1 to 8 carbon atoms (methyl, methoxymethyl, ethyl, ethoxymethyl, iodoethyl, propyl, isopropyl, butyl, isobutyl, ethoxyethyl, methylthioethyl, methanesulfonylethyl, trichloroethyl, t-butyl, and so on), an alkenyl having 3 to 8 carbon atoms (propenyl, allyl, prenyl, hexenyl, phenylpropenyl, dimethylhexenyl, and so on), an aralkyl having 7 to 19 carbon atoms (benzyl, methylbenzyl, dimethylbenzyl, methoxybenzyl, ethoxybenzyl, nitrobenzyl, aminobenzyl, diphenylmethyl, phenylethyl, trityl, di-t-butylhydroxybenzyl, phthalidyl, phenacyl, and so on), an aryl having 6 to 12 carbon atoms (phenyl, tolyl, methoxyphenyl, diisopropylphenyl, xylyl, trichlorophenyl, pentachlorophenyl, indanyl, and so on), an ester formed with N-hydroxyamino compound having 1 to 12 carbon atoms (ester formed with acetone oxime, acetophenone oxime, acetaldoxime, N-hydroxy succinimide, N-hydroxy phthalimide), a hydrocarbonated silyl having 3 to 12 carbon atoms (trimethyl silyl, dimethyl methoxy silyl, t-butyl dimethyl silyl, and so on), a hydrocarbonated stannyl having 3 to 12 carbon atoms (trimethyl stannyl, and so on), mono-oxygenated alkyl having 2–15 carbon atoms [a straight, branched, cyclic or partially cyclic alkanoyloxy-alkyl (acetoxymethyl, acetoxyethyl, propionyloxymethyl, pivaloyloxymethyl, pivaloyloxyethyl, cyclohexanacetoxyethyl, cyclohexanecarbonyloxycyclohexylmethy, and so on), an alkoxycarbonyloxyalkyl having 3 to 15 carbon atoms (ethoxycarbonyloxyethyl, isopropoxycarbonyloxyethyl, isopropoxycarbonyloxypropyl, t-butoxycarbonyloxyethyl, isopentyloxycarbonyloxypropyl, cyclohexyloxycarbonyloxyethyl, cyclohexylmethoxycarbonyloxyethyl, bornyloxycarbonyloxyisopropyl, and so on), an alkoxyalkyl having 2 to 8 carbon atoms (methoxymethyl, methoxyethyl, and so on), 2-oxacycloalkyl having 4 to 8 carbon atoms (tetrahydropyranyl, tetrahydrofurany ester, and so on), and so on], a substituted aralkyl having 8 to 12 carbon atoms (phenacyl, phthalidyl, and so on), an aryl having 6 to 12 carbon atoms (phenyl, xylyl, indanyl, and so on), an alkenyl having 2 to 12 carbon atoms (allyl, (2-oxo-1,3 -dioxolyl) methyl, and so on), and so on. The protected group moiety may have any further substituents.

An "amino-protecting group" includes those which are usually used in the art, and the preferred amino-protecting groups include acyl derivatives such as benzoyl, acetyl, formyl, trifluoroacetyl, and so on, urethane type derivatives such as benzyloxycarbonyl, t-butoxycarbonyl, isopropoxycarbonyl, methoxycarbonyl, and so on, or alkyl derivatives such as allyl, benzyl, trityl, tetrahydropyranyl, and so on.

The compounds of the present invention can form salts with a metal such as an alkali metal (sodium, pottasium, etc.), or an alkaline earth metal (calcium, etc.), which may form a salt with a carboxylic acid.

The compounds of the present invention can be prepared by coupling a dicarboxylic acid derivative of the formula:

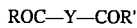

wherein

R and R' are independently hydroxy, halogen, or ester residue, with an alcohol of the formula:

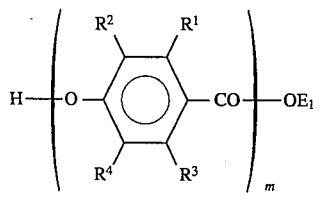

and/or

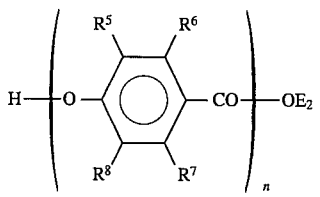

wherein $R^1$, $R^2$, $R^3$, $R^4$, $R^5$, $R^6$, $R^7$, $R^8$, $E_1$, $E_2$, m, and n are as defined above, and if necessary, conducting the deesterification.

The present compounds can be formulated into oral or external preparations in association with various carriers. The dose of the compounds will differ depending on the intended treatment effect, the administration route, and age and body weight of particular patients, and therefore, it is difficult to define the dose in general. As a whole, daily dose may be about 0.1 mg to about 500 mg, preferably 0.5 mg to about 100 mg in the case of oral administration. On the administration, the above dose may be divided into one to five portions.
Typical examples of the compounds of the present invention, which are shown in the above formula are illustrated below:
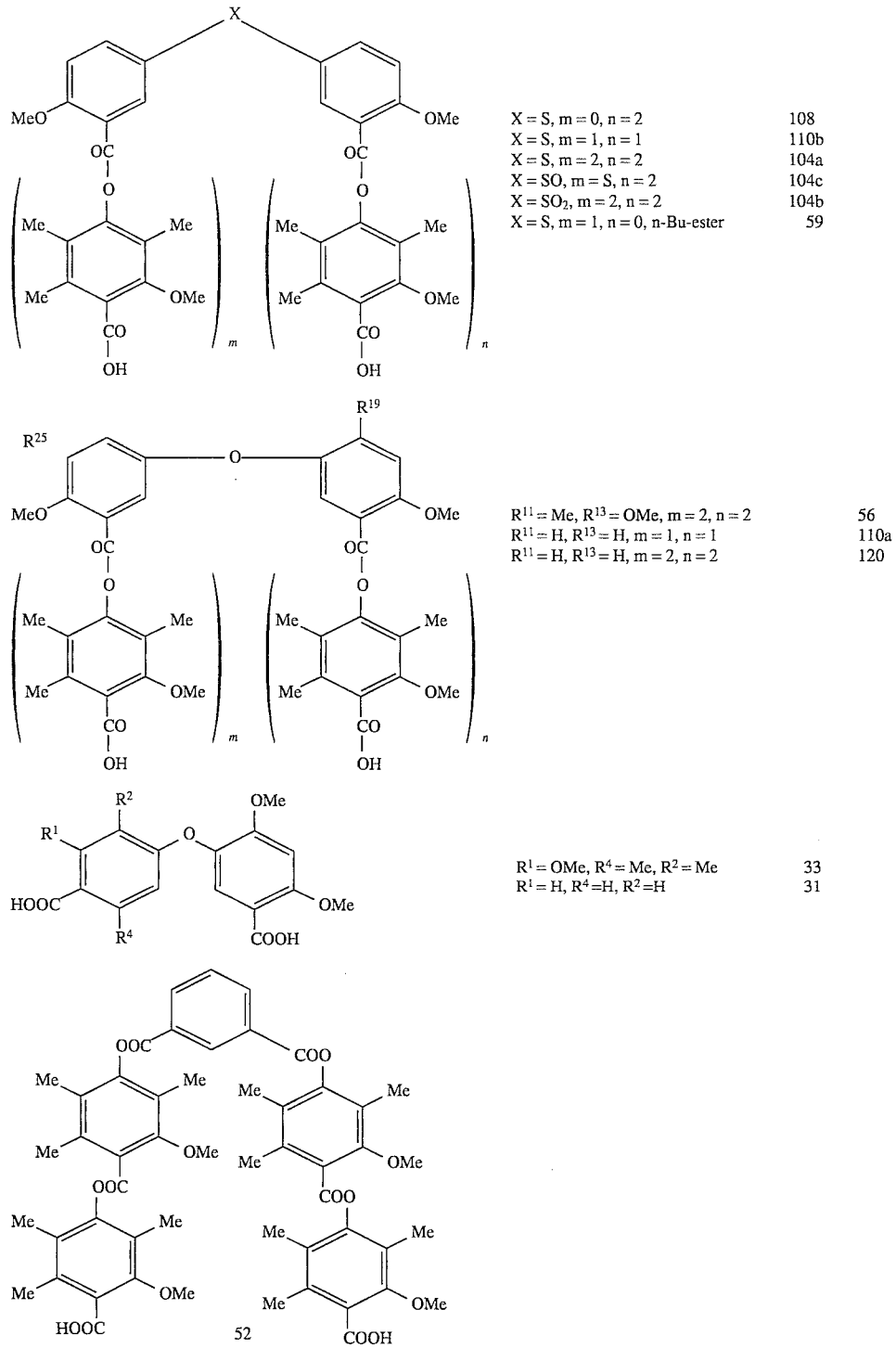

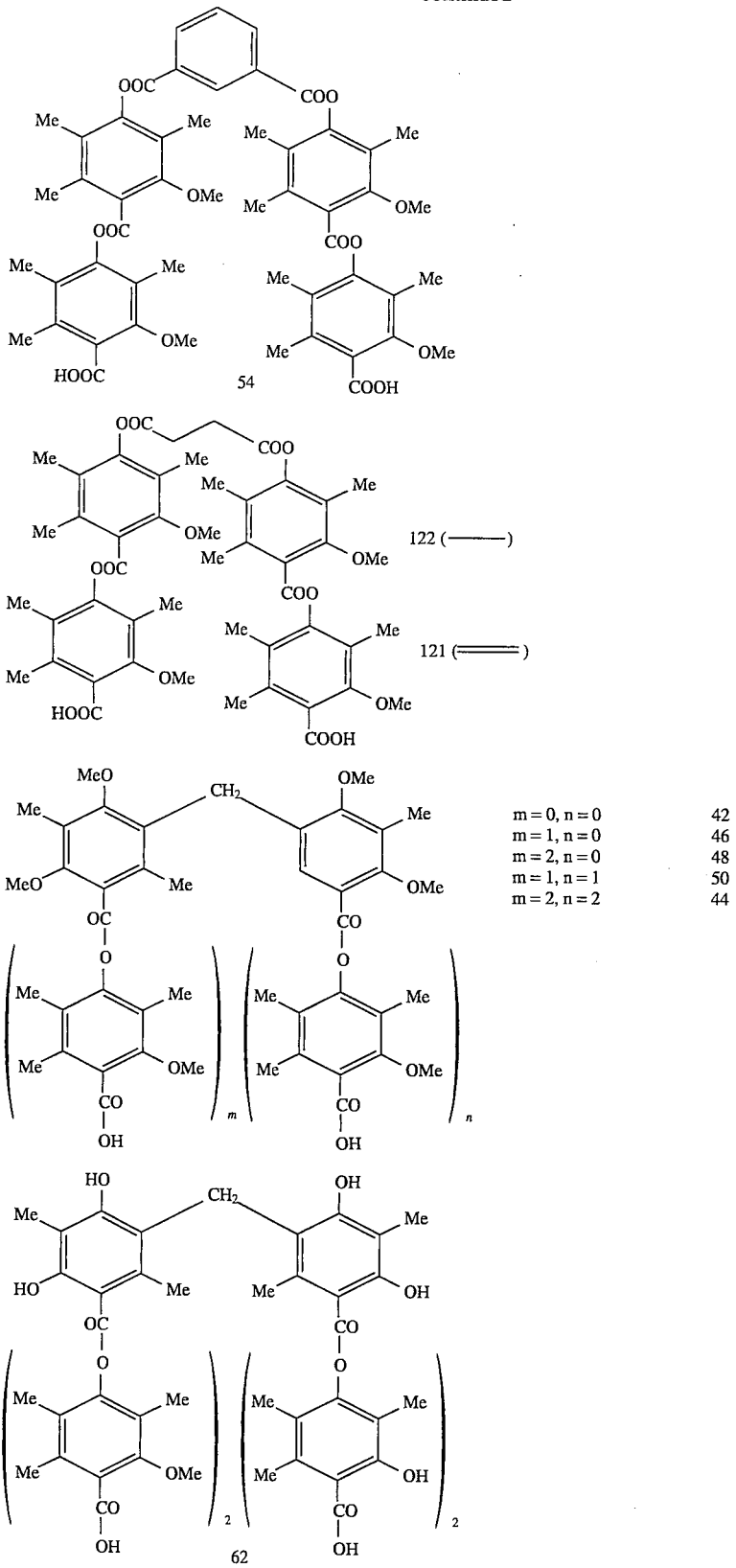

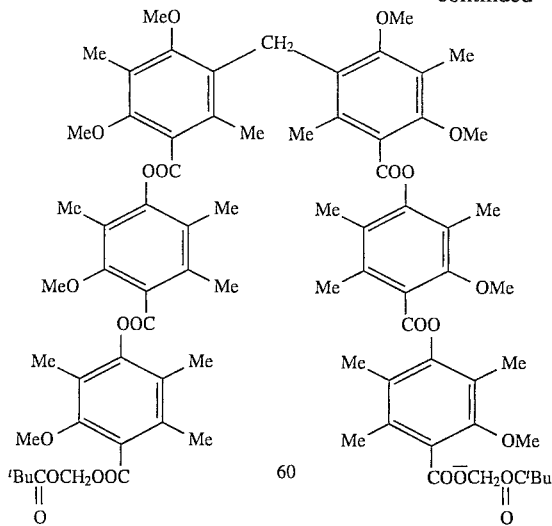

According to one further aspect of the present invention, there is provided another class of the following compounds which also exhibit phospholipase $A_2$ inhibitory effect:

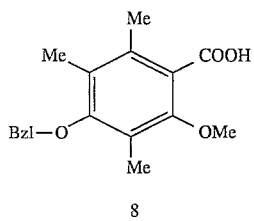

8

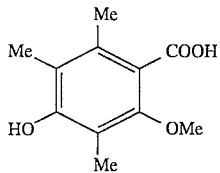

9

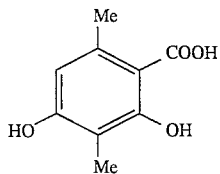

10

All of the compounds of the present invention can be prepared by various methods which are known in the art. The following Examples and Preparations are provided to further illustrate the process for preparing the compounds of the invention.

Preparation 1

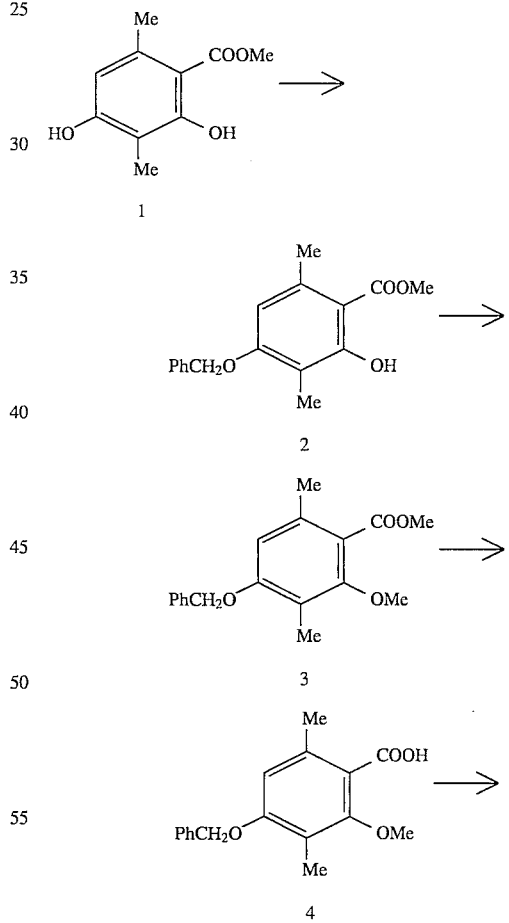

Preparation 1

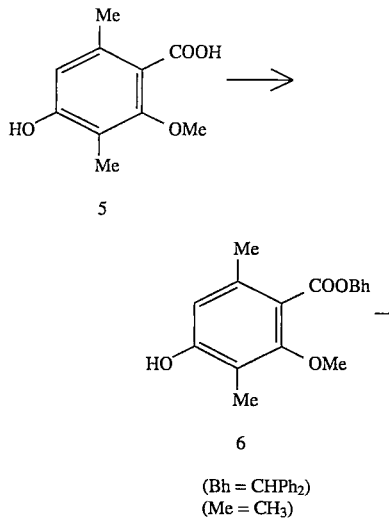

(Bh = CHPh₂)
(Me = CH₃)

[Step 1] (1→2)

A mixture containing the compound 1 (5.0 g, 25.5 mM), which is known in literatures, PhCH₂Br (3.2 ml, 25.5 mM×1.06), K₂CO₃ (8.8 g, 25.5 mM×2.5), and 200 ml of acetone was stirred at room temparature for 23 hours, and then the resultant solid was filtered off. The filtrate was distributed between ethyl acetate and 2N hydrochloric acid, and the organic phase was washed With water, dried over Na₂SO₄, and then concentrated in vacuo to yield the crude compound 2. The compound was recrystallized from ether—n-hexane to provide 4.8 g of the benzylated compound 2 (66%). Colorless needle crystal. M.p: 77°–78° C. TLC (Rf: 0.6, Developer: n-hexane—ethyl acetate (4:1)).

¹HNMR (CDCl₃): δ2.15 (s,3H), 2.51 (s,3H), 3.92 (s,3H), 5.12 (s,2H), 6.34 (s,1H), 7.28–7.50 (m,5H), 11.84; IR (Nujol): 1648, 1577, 803 cm⁻¹; Elementary Analysis (for C₁₇H₁₈O₄), Theory: C,71.31; H,6.34 (%); Found: C,70.99; H,6.32 (%).

[Step 2](2→3)

A mixture containing the compound 2 (4.8 g, 16.8 mM), Me₂SO₄ (4.74 ml, 16.8 mM×3), K₂CO₃ (11.58 g, 16.8 mM×5), and 200 ml of acetone was heated under reflux for two hours, and, after cooling, the resultant solid was filtered off. The filtrate was distributed between ethyl acetate and 2N hydrochloric acid, and the organic phase was washed with water, dried over Na₂SO₄, and then concentrated in vacuo to yield the crude product 3. The product was recrystallized from ether—n-hexane to provide 5.04 g of the compound 3 (100%). Colorless needle crystal. M.p: 56°–57° C. TLC (Rf: 0.5, Developer: n-hexane—ethyl acetate (4:1)).

¹HNMR (CDCl₃): δ2.17 (s,3H), 2.29 (s,3H), 3.77 (s,3H), 3.90 (s,3H), 5.07 (s,2H), 6.54 (s,1H), 7.24–7.50 (m,5H); IR (Nujol); 1725, 1605, 1580, 760, 703 cm⁻¹; Elementary Analysis (for C₁₈H₂₀O₄), Theory: C,71.98; H,6.71 (%); Found: C,71.97; H,6.90 (%).

[Step 3](3→4)

Compound 3 (5.04 g, 16.8 mM) was dissolved in 68.2 ml of DMSO, and KOH (5.64 g, 16.8 mM×6) which had been dissolved in 13.6 ml of water at 0° C. was added to the solution, and then the mixture was stirred overnight at 90° C. After cooling, the mixture was poured into 2N hydrochloric acid with ice, and the resultant mixture was extracted with ether. The organic phase was washed with water, and then dried, concentrated in vacuo to yield the crude product 4. The product was recrystallized from ether—n-hexane to provide 4.44 g of the compound 4 (93%). Colorless flaky crystal. M.p: 124°–125° C. TLC (Rf: 0.3, Developer: chloroform—methanol (9:1)).

¹HNMR (CDCl₃): δ2.20 (s,3H), 2.56 (s,3H), 3.85 (s,3H), 5.12 (s,2H), 6.65 (s,1H), 7.25–7.50 (m,5H); IR (Nujol): 2200–3360, 1685, 1600, 1567, 1170, 1115 cm⁻¹; Elementary Analysis (for C₁₇H₁₈O₄), Theory: C,71.31; H,6.34 (%); Found: C,71.30; H,6.44 (%).

[Step 4](4→5)

A mixture containing the compound 4 (4.34 g, 15.2 mM), Pd—C (800 mg), 25 ml of ethyl acetate, and 6 ml of methanol was subject to hydrogenation by passing hydrogen gas (340 ml, 15.2 mM) through the mixture. After the catalyst was filtered off, the solution was concentrated in vacuo to yield 2.97 g of the colorless crystals 5 (100%). M.p: 153°–155° C. TLC (Rf: 0.25, Developer: chloroform—methanol (9:1)).

¹HNMR (CD₃OD): δ2.08 (s,3H), 2.24 (s,3H), 3.74 (s,3H), 6.44 (s,1H); IR (Nujol): 2200–3440, 3200, 1715, 1610, 1588, 1263, 1155 cm⁻¹; Elementary Analysis (for C₁₀H₁₂O₄), Theory: C,61.22; H,6.17 (%); Found: C,61.02:H,6.22 (%).

[Step 5](5→6)

Compound 5 (2.97 g, 15.2 mM) was dissolved in 30 ml of ethyl acetate, and diphenyldiazomethane (5.89 g, 2 mM×2) was added thereto at room temperature, and the mixture was left stand overnight. An excess of diphenyldiazomethane was decomposed by adding 2N hydrochloric acid thereto, and the resultant mixture was extracted with ethyl aceatate. The organic phase was washed with water, dried, and then concentrated in vacuo. The residue was subjected to column chromatography (80 g of SiO₂, eluent: n-hexane—ethyl acetate (19:1) to (1:1)) to yield the benzhydryl ester 6. The product was recrystallized from ether—n-hexane to yield 3.76 g of 6 as a colorless crystal (69%). M.p: 96°–97° C. TLC (Rf: 0.25, Developer: n-hexane—ethyl acetate (4:1)).

¹HNMR (CDCl₃): δ2.12 (s,6H), 3.54 (s,3H), 4.97 (s,1H), 6.39 (s,1H), 7.15 (s,1H), 7.21–7.50 (m,10H); IR (Nujol): 3410, 1686, 1610, 1590, 1160, 1095 cm⁻¹; Elementary Analysis (for C₂₃H₂₂O₄), Theory: C,76.22; H,6.12 (%); Found: C,76.31; H,6.12 (%).

Preparation 2

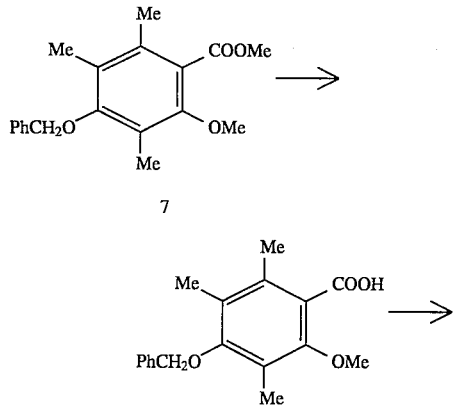

13
-continued
Preparation 2

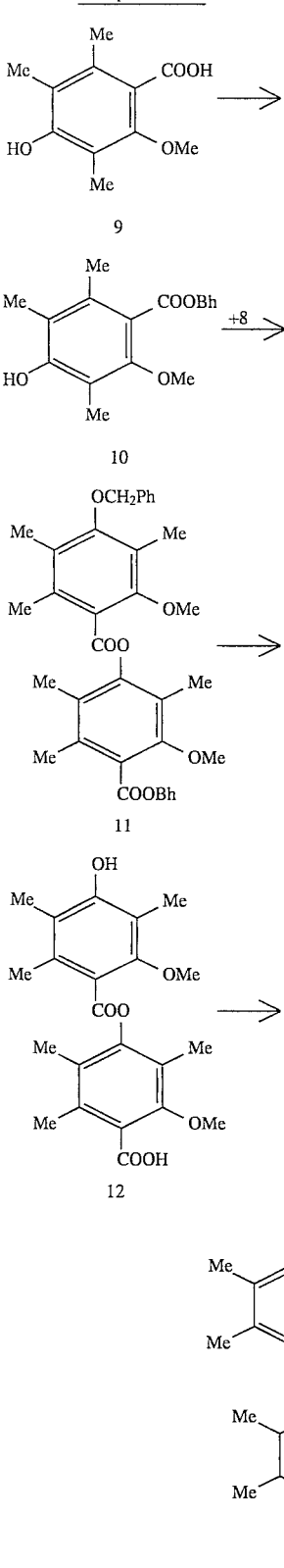

[Step 1](7→8)

Compound 7 (12.7 g, 40.4 mM), which is known in the literature, was hydrolyzed in a similar procedure to that of Step 3 in Preparation 1, to yield 11.7 g of the compound 8 as a colorless crystal (97%). M.p. 122°–130° C.

14

$^1$HNMR (CDCl$_3$): δ2.22 (s,3H), 2.23 (s,3H), 2.33 (s,3H), 3.82 (s,3H), 4.78 (s,2H), 7.28–7.55 (m,5H); IR (KBr): 3650–2250, 3430, 2950, 1687, 1222, 1105, 737, 693 cm$^{-1}$; Elementary Analysis (for C$_{18}$H$_{20}$O$_4$), Theory: C,71.98; H,6.71 (%); Found: C,72.17; H,6.76 (%).

[Step 2](8→9)

Compound 8 (5.0 g, 16.6 mM) was subject to hydrogenation by a similar procedure to that of Step 4 in Preparation 1, to yield 3.8 g of the compound 9 as a colorless crystal (97%). M.p. 130°–132° C. TLC (Rf: 0.4, Developer: chloroform—methanol (9:1)).

$^1$HNMR (CDCl$_3$): δ2.16 (s,3H), 2.19 (s,3H), 2.35 (s,3H), 3.81 (s,3H); IR (KBr): 3660–2100, 3320, 1714, 1562, 1380, 1205 cm$^{-1}$; Elementary Analysis (for C$_{11}$H$_{14}$O$_4$), Theory: C,62.85; H,6.71 (%); Found: C,62.58; H,6.65 (%).

[Step 3] (9→10)

Compound 9 (3.36 g, 16.0 mM) was benzhydrylated by a similar procedure to that of Step 5 in Preparation 1, to yield 5.76 g of the ester 10. (96%). Colorless pillar crystals. M.p. 125°–127° C. TLC (Rf: 0.2, Developer: n-hexane—ethyl acetate (4:1)).

$^1$HNMR (CDCl$_3$): δ2.06 (s,3H), 2.11 (s,3H), 2.15 (S,3H), 3.52 (s,3H), 4.82 (s,1H), 7.17 (s,1H), 7.22–7.50 (m,10H); IR (Nujol): 3360, 1695, 1585, 1290, 1205 cm$^{-1}$; Elementary Analysis (for C$_{24}$H$_{24}$O$_4$), Theory: C,76.57; H,6.43 (%); Found: C,76.49; H,6.55 (%).

[Step 4] (8+10→11)

The compound 8 (4.19 g, 13.28 mM×1.05) was dissolved in 20 ml of CH$_2$Cl$_2$, and oxalyl chloride (4.25 ml, 13.28 mM×1.05×3.5) was added thereto at room temperature, and the resultant mixture was stirred at room temperature for 30 minutes, and then the mixture was gently warmed under reflux for 30 minutes. After concetrated in vacuo, the residue was dissolved in THF, and the solution was again concentrated in vacuo. Alternatively, compound 10 (5.00 g, 13.28 mM) was dissolived in 20 ml of THF, and n-BuLi (1.6M solution in hexane, 8.30 ml, 13.28 mM) was added gradually to the solution at –78° C., and then the solution was stirred at the same temperature for 30 minutes. To the reaction mixture was added a solution of the acid chloride 8 obtained above in THF (30 ml) at –78° C., and the mixture was stirred at the same temperature for 10 minutes. The mixture was allowed to warm slowly to room temperature, and left stand overnight. The reaction mixture was distributed between ethyl acetate and 1N hydrochloric acid, and the organic phase was washed with water, and then dried. After the mixture was concentrated in vacuo, the residue was subjected to column chromatography (200 g of SiO$_2$, eluent: toluene—ethyl acetate (0%–10%)) to yield 7.32 g of 11 as a colorless crystal (84%). M.p: 183°–185° C. TLC (Rf: 0.7, Developer: benzene—ethyl acetate (9:14).

$^1$HNMR (CDCl$_3$): δ2.09 (s,3H), 2.22 (s,3H), 2.25 (s,3H), 2.26 (s,3H), 2.28 (s,3H), 2.37 (s,3H), 3.58 (s,3H), 3.81 (s,3H), 4.80 (s,2H), 7.20 (s,1H), 7.28–7.55 (m,15H); IR (Nujol): 1760, 1723, 1573, 1455, 1156, 740, 697 cm$^{-1}$; Elementary Analysis (for C$_{42}$H$_{42}$O$_7$), Theory: C,76.57; H,6.43 (%); Found: C,76.83; H,6.55 (%).

[Step 5] (11→12)

Compound 11 (7.32 g, 11.1 mM) was subject to hydrogenation by a similar procedure to that of Step 4 in Preparation 1, and the resultant crude compound 12 was recrystallized from toluene—n-hexane to yield 4.31 g of 12 as a colorless crystal (96%). M.p. 207°–209° C. TLC (Rf: 0.2, Developer: chloroform—methanol (9:1)).

$^1$HNMR (DMSO): δ2.10–2.30 (m,18H), 3.69 (s,3H), 3.71 (s,3H), 8.70–8.93 (brs,1H); IR (KBr): 3650–2260, 3500, 1750, 1576, 1460, 1410, 1170 cm$^{-1}$; Elementary Analysis (for C$_{22}$H$_{26}$O$_7$), Theory: C,65.66; H,6.51 (%); Found: C,65.50; H,6.58 (%).

[Step 6] (12→13)

Compound 12 (4.31 g, 10.7 mM) was benzhydrylated by a similar procedure to that of Step 5 in Preparation 1, and the resultant compound was recrystallized from ether—n-hexane to yield 5.31 g of 13 (87%). Colorless pillar crystal. M.p. 195°–197° C. TLC (Rf: 0.4, Developer: toluene—ethyl acetate (9:1)).

$^1$HNMR (CDCl$_3$): δ2.08 (s,3H), 2.19–2.24 (m,12H), 2.37 (s,3H), 3.56 (s,3H), 3.80 (s,3H), 4.95 (s,1H), 7.19 (s,1H), 7.28–7.52 (m,10H); IR (Nujol): 3390, 1737, 1706, 1285, 1156, 759, 700 cm$^{-1}$; Elementary Analysis (for C$_{35}$H$_{36}$O$_7$), Theory: C,73.92; H,6.38 (%); Found: C,73.75; H,6.41 (%).

Preparation 3

14→16

5-Bromo-2,4-dihydroxy benzoic acid, mono-hydrade 14 (10 g, 39.8 mM) was benzhydrylated by a similar procedure to that of Step 5 in Preparation 1, to yield 15, and the latter compound was dimethoxylated by the procedure of Step 2 in Preparation 1 to yield 16 as a crude cystals. The resultant compound was recrystallized from ether—n-hexane to yield 13.6 g of 16 (80%). Colorless pillar crystals. M.p. 124°–125° C. TLC (Rf: 0.2, Developer: n-hexane—ethyl acetate (4:1)).

$^1$HNMR (CDCl$_3$): δ3.94 (s,3H), 3.95 (s,3H), 6.48 (s,1H), 7.07 (s,1H), 7.21–7.48 (m,10H), 8.16 (s,1H); IR (Nujol): 1708, 1600, 1248, 1214, 1029 cm$^{-1}$; Elementary Analysis (for C$_{22}$H$_{19}$O$_4$Br), Theory: C,61.84; H,4.48; Br,18.70 (%); Found: C,61.85; H,4.61; Br,18.43 (%).

Preparation 4

[Step 1] (1→17)

Compound 1 (5.0 g, 25.5 mM), which is known in literatures, was suspended in 50 ml of 1,2-dichloroethane, and 10 ml of a solution of bromine (945 μl, 25.5 mM×1.2) in 1,2-dichloroethane was added to the suspension, and the mixture was stirred overnight. The mixture was diluted with chloroform, and then the solution was washed with water, 5% aqueous sodium sulfite, and water successively in this order, and then dried. After concentrated in vacuo, the residue was subjected to column chromatography (90 g of SiO$_2$, eluent: n-hexane—ethyl acetate (9:1) to (2:1)) to yield 17. The resultant compound was recrystallized from ether—n-hexane to yield 5.64 g of 17 (80%). Colorless pillar crystals. M.p. 87°–88° C. TLC (Rf: 0.75, Developer: n-hexane—ethyl acetate (4:1)).

$^1$HNMR (CDCl$_3$): δ2.18 (s,3H), 2.64 (s,3H), 3.95 (s,3H), 6.15 (s,1H), 11.63 (s,1H); IR (Nujol): 3440, 3420, 1655, 1607, 1265 cm$^{-1}$; Elementary Analysis (for C$_{10}$H$_{11}$O$_4$Br), Theory: C,43.66; H,4.03; Br,29.05 (%); Found: C,43.63; H,4.08; Br,29.13 (%).

[Step 2] (17→19)

Compound 17 (5.72 g, 20.8 mM) was dimethoxylated by the same procedure of Step 2 in Preparation 1 to yield the crude compound 18, which was directly hydrolyzed by the same procedure of Step 3 in Preparation 1 to yield the crude compound 19. The compound was recrystallized from petroleum ether to yield 4.69 g of the compound 19 (78%). Colorless needle crystal. M.p. 115°–116° C. TLC (Rf: 0.7, Developer: 1% acetic acid—ethyl acetate).

$^1$HNMR (CDCl$_3$): δ2.28 (s,3H), 2.47 (s,3H), 3.82 (s,3H), 3.83 (s,3H); IR (Nujol): 3380–2000, 1690, 1582, 1556, 1303, 1105, 680 cm$^{-1}$; Elementary Analysis (for C$_{11}$H$_{13}$O$_4$Br), Theory: C,45.70; H,4.53; Br,27.64 (%); Found: C,45.81; H,4.62; Br,27.37 (%).

[Step 3] (19→20)

Compound 19 (1.30 g, 4.50 mM) was benzhydrylated by a similar procedure to that of Step 5 in Preparation 1, and the resultant compound was subjected to column chromatography (60 g of SiO$_2$, eluent: n-hexane—ethyl acetate (10:0) to (9:1)) to yield 20 as a crystal, which was recrystallized from ethyl acetate—hexane to yield 1.87 g of 20 (91%). Colorless pillar crystals. M.p. 136°–137° C. TLC (Rf: 0.6, Developer: n-hexane—ethyl acetate (4:1)).

¹HNMR (CDCl₃): δ2.19 (s,3H), 2.24 (s,3H), 3.54 (s,3H), 3.78 (s,3H), 7.12 (s,1H), 7.24–7.46 (m,10H); IR (Nujol): 1725, 1266, 1160, 743, 699 cm⁻¹.

Preparation 5

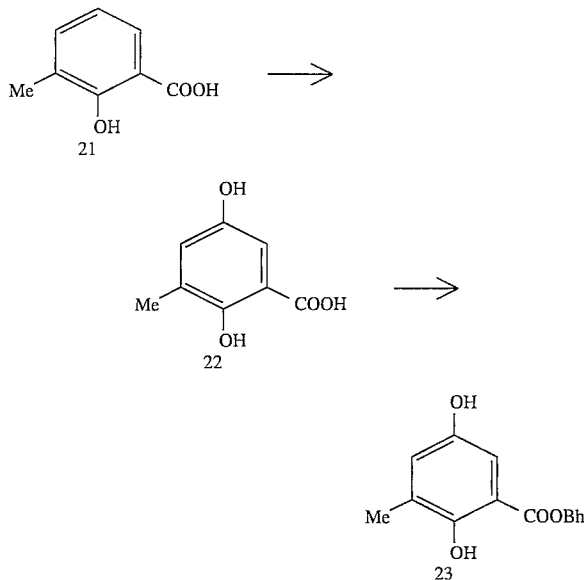

2-Hydroxy-3-methyl benzoic acid 21 (20 g, 131 mM) was dissolved in an aqueous sodium hydroxide (32 g of NaOH, 335 ml of water), and 260 ml of a solution of K₂S₂O₈ (40 g, 131 mM×1.31) in water was added thereto at 0° C. The reaction was stirred at room temperature for four hours, and then left stand over four days. The addition of dilute sulfuric acid (44 ml of sulfuric acid, 300 ml of water) resulted in the appearance of brown precipitates. The precipitates were filtered off, and then the filtrate was heated under reflux for 9 hours. After cooling, the solution was partitioned by adding ethyl acetate and NaCl, and the organic phase was passed through the small amount of silica gel (40 g), and the resultant elution was concentrated to yield 22 as a brown crystalline powder. The powder was benzhydrylated by a procedure similar to that of Step 5 in Preparation 1, and the resultant compound was subjected to column chromatography (150 g of SiO₂, eluent: n-hexane—ethyl acetate (9:1)) to yield 15.2 mg of 23 (34.8%). Pale yellow gummy material.

¹HNMR (CDCl₃): δ2.22 (s,3H), 4.55 (brs,1H), 6.90 (d,J= 3.2 Hz,1H), 7.09 (s,1H), 7.26–7.50 (m,11H), 10.50 (s,1H).

Preparation 6

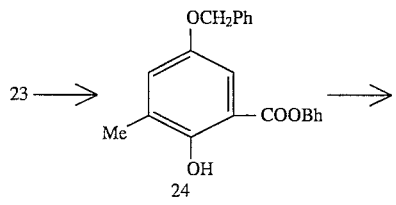

-continued
Preparation 6

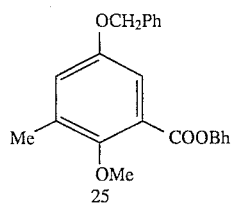

Compound 23 (7.6 g, 22.7 mM) was benzylated by a similar procedure to that of Step 1 in Preparation 1, to yield the crude compound 24. The compound was subjected to column chromatography (150 g of SiO₂, eluent: n-hexane ethyl acetate (9:1)) to yield 8.1 g of 24 as a pale yellow oil (84.4%). Subsequently, the resultant compound was methoxylated by the procedure of Step 2 in Preparation 1 to yield the crude compound 25. The compound was subjected to column chromatography (150 g of SiO₂, eluent: n-hexane ethyl acetate (9:1) to (4:1)) to yield 7.77 g of 25 as a pale yellow oil (92%). TLC (Rf: 0.4, Developer: n-hexane ethyl acetate (4:1)).

¹HNMR (CDCl₃): δ2.29 (s,3H), 3.66 (s,3H), 5.03 (s,2H), 6.99 (d,J=3.0 Hz,1H), 7.12 (s,1H), 7.20–7.50 (m,16H).

Preparation 7

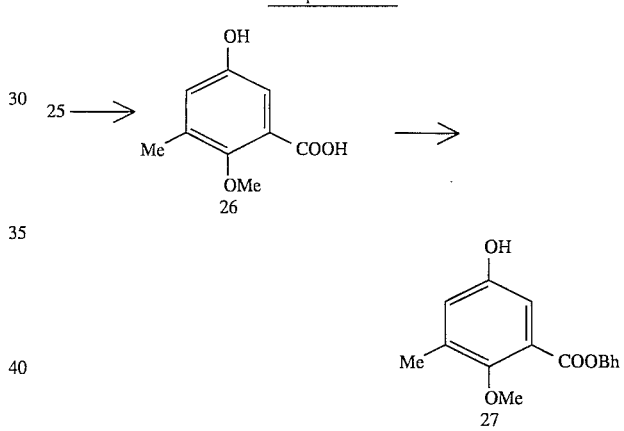

[Step 1] (25→26)

Compound 25 (7.53 g, 17.2 mM) was subject to hydrogenation by a similar procedure to that of Step 4 in Preparation 1, to yield 26 as a crude crystal. The compound was recrystallized from ether—petroleum ether to yield 2.83 g of 26 (90%). Colorless prism crystals. M.p. 142°–144° C. TLC (Rf: 0.5, Developer: ethyl acetate acetic acid (1%)).

¹HNMR (DMSO): δ2.17 (s,3H), 3.64 (s,3H), 6.77 (d,J= 3.0 Hz,1H), 6.87 (d,J=3.0 Hz,1H), 9.34 (brs,1H); IR (Nujol): 3320, 1679, 1606 cm⁻¹; Elementary Analysis (for C₉H₁₀O₄), Theory: C,59.34; H,5.53 (%); Found: C,59.32; H,5.56 (%).

[Step 2] (26→27)

Compound 26 (2.62 g, 14.4 mM) was benzhydrylated by a similar procedure to that of Step 5 in Preparation 1, to yield the crude compound 27. The compound was purified by column chromatography (150 g of SiO₂, eluent: n-hexane—ethyl acetate (19:1) to (2:1)), and the resultant compound was crystallized from ether—petroleum ether to yield 3.45 g of 27 (69%). Colorless prism crystals. M.p. 101°–103° C. TLC (Rf: 0.4, Developer: benzene—ethyl acetate (9:1)).

¹HNMR (CDCl₃): δ2.27 (s,3H), 3.66 (s,3H), 4.92 (s,1H), 6.85 (d,J=3 Hz,1H), 7.12 (s,1H), 7.18 (d,J=3 Hz,1H), 7.21–7.50 (m,10H); IR (Nujol): 3430, 1689 cm⁻¹; Elementary Analysis (for $C_{22}H_{20}O_4$), Theory: C,75.84; H,5.79 (%); Found: C,75.89; H,5.81 (%).

Preparation 8

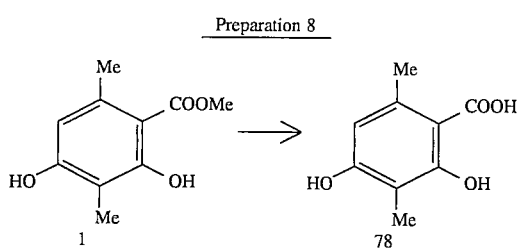

Synthesis of 78

To compound 1 (1.00 g, 51.0 mM), which is known in the literatures, was added ice-cooled conc. sulfuric acid (30 ml), and the mixture was left stand overnight. The mixture was poured onto ice, and extracted with ether. The ether phase was extracted with an aqueous saturated sodium bicarbonate, and the water phase was acidified with 2N hydrochloric acid and extracted again with ether. The extract was washed with water, dried, and then concentrated in vacuo, to yield 7.63 g of 78 as a colorless crystal (82%). M.p. 190°–192° C. TLC (Rf: 0.2, Developer: chloroform—methanol (9:1)).

$^1$HNMR (DMSO): δ1.93 (s,3H), 2.40 (s,3H), 3.36 (brs, 1H), 6.26 (s,1H), 10.05 (s,1H), 12.90 (brs,1H); IR (KBr): 3660–2080, 3410, 1639, 1458, 1262, 1175, 1091 cm$^{-1}$; Elementary Analysis (for $C_9H_{10}O_4$), Theory: C,59.34; H,5.53 (%); Found: C,59.25; H,5.56 (%).

Preparation 9

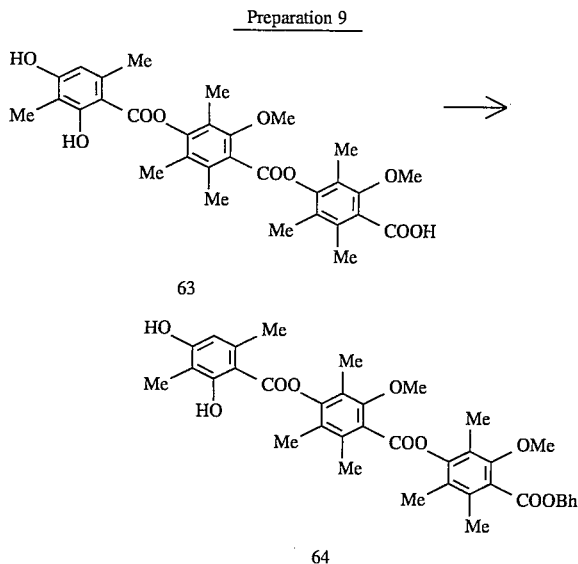

Synthesis of 64

Compound 63 (1.00 g, 1.76 mM) was benzhydrylated by a similar procedure to that of Step 5 in Preparation 1, to yield the crude compound 64. The compound was crystallized from ethyl acetate—n-hexane to yield 765 mg of 64 as a colorless crystal (59%). M.p. 198°–200° C. TLC (Rf: 0.2, Developer: n-hexane—ethyl acetate (4:1)).

$^1$HNMR (CDCl$_3$): δ2.02–2.28 (m,18H), 2.40 (s,3H), 2.65 (s,3H), 3.57 (s,3H), 3.83 (s,3H), 5.44 (s,1H), 6.32 (s,1H), 7.20 (s,1H), 7.28–7.50 (m,10H), 11.86 (s,1H).

EXAMPLE 1

4-Carboxyphenyl (5'-Carboxy-2',4'-dimethoxyphenyl) Ether

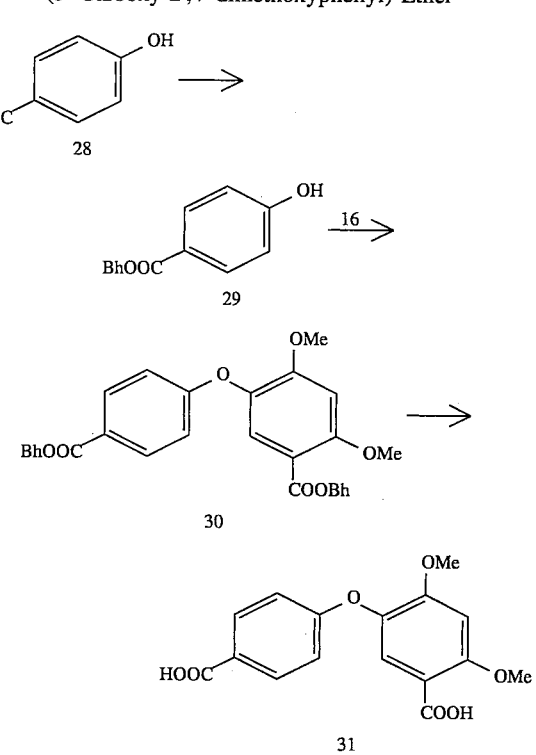

[Step 1] (28→29)

4-Hydroxy benzoic acid 28 (2.76 g, 20 mM) was benzhydrylated in a similar procedure to that of Step 5 in Preparation 1, to yield the crude compound 29. The compound was recrystallized from methylene chloride—toluene to yield 4.47 g of 29 (74%).

M.p. 135°–137° C. TLC (Rf: 0.2, Developer: n-hexane—ethyl acetate (4:1)). $^1$HNMR (CDCl$_3$): δ5.63 (s,1H), 6.80–6.90 (m,A$_2$B$_2$ A-Part,2H), 7.08 (s,1H), 7.21–7.48 (m,10H), 7.98–8.12 (m,A$_2$B$_2$ B-Part,2H).

[Step 2] (29+16→30)

Compound 29 (1.61 g, 5.29 mM) was dissolved in 15 ml of DMF, and to the solution was added NaH (212 mM, 5.29 mM) in a stream of argon at 0° C. After the mixture was stirred at room temperature for 30 minutes, a complex of copper bromide dimethyl sulfide (3.26 g, 5.29 mM×3) was added thereto, and the mixture was stirred for a while. Compound 16 (2.26 g, 5.29 mM) was added thereto, and then the mixture was stirred at 160° C. for about 20 hours. After cooling, the resultant mixture was distributed between ethyl acetate and 2N hydrochloric acid, and the organic phase was washed with hydrochloric acid three times, water, and then dried, concentrated in vacuo, and the residue was subjected to column chromatography (70 g of SiO$_2$, eluent: n-hexane—ethyl acetate (9:1) to (1:1)), to yield 180 mg of 30 as an oil (5%).

TLC (Rf: 0.2, Developer: n-hexane—ethyl acetate (4:1)). $^1$HNMR (CDCl$_3$): δ3.84 (s,3H), 3.97 (s,3H), 6.59 (s,1H), 6.85–6.94 (m,A$_2$B$_2$ A-part,2H), 7.06 (s,1H), 7.09 (s,1H), 7.18–7.48 (m,20H), 7.77 (s,1H), 8.03–8.12 (m,A$_2$B$_2$ B-part, 2H)

[Step 3] (30→31)

A mixture containing 30 (180 mg, 277 mM), trifluoroacetic acid (1 ml), and anisole (0.5 ml) was stirred at room temperature for 30 minutes, and after concentration in vacuo, the residue was crystallized by adding ether thereto, to yield 62 mg of 31 (70%).

M.p. 237°–239° C. TLC (Rf: 0.4, Developer: ethyl acetate—acetic acid (1%)). $^1$HNMR (DMSO): δ3.86 (s,3H), 3.99 (s,3H), 6.80–6.90 (m,$A_2B_2$ A-part,2H), 6.85 (s,1H), 7.64 (s,1H), 7.90–8.00 (m,$A_2B_2$ B-part,2H); IR (KBr): 3680–2320, 3300, 1725, 1675, 1618, 1230, 1023 cm$^{-1}$; Elementary Analysis (for $C_{16}H_{14}O_7$), Theory: C,60.38; H,4.43 (%); Found: C,60.12; H,4.70 (%).

EXAMPLE 2

4-Carboxy-3-methoxy-2,5-dimethylphenyl (5'-carboxy-2',4'-dimethoxyphenyl) Ether

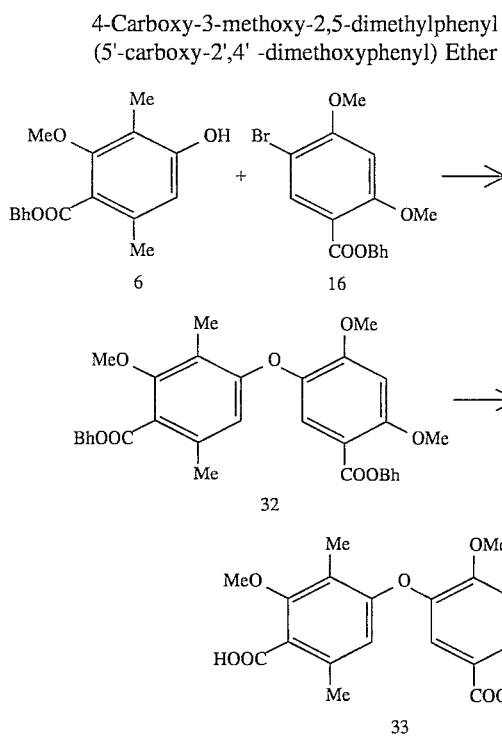

[Step 1] (6+16→32)

Compound 6 (2.0 g, 5.52 mM), and 16 (2.36 g, 5.52 mM) were treated in a similar procedure to that of Step 2 in Expample 1, to yield the crude compound 32. The compound was subjected to column chromatography (90 g of $SiO_2$, eluent: n-hexane—ethyl acetate (9:1) to (1:1)), to yield 670 mg of 32 as an oil (17%).

TLC (Rf: 0.2, Developer: n-hexane—ethyl acetate (4:1)); $^1$HNMR (CDCl$_3$): δ2.04 (s,3H), 2.24 (s,3H), 3.58 (s,3H), 3.86 (s,3H), 3.96 (s,3H), 6.16 (s,1H), 6.58 (s,1H), 7.05 (s,1H), 7.16 (s,1H), 7.18–7.58 (m,20H), 7.63 (s,1H).
[Step 2] (32→33)

Compound 32 (670 mg, 945 μM) was treated in a similar procedure to that of Step 3 in Expample 1, to yield mg of 33 as a colorless crystal (81%).

M.p. 199°–200° C., TLC (Rf: 0.5, Developer: ethyl acetate—acetic acid (1%)); $^1$HNMR (DMSO): δ2.10 (s,3H), 2.14 (s,3H), 3.73 (s,3H), 3.87 (s,3H), 3.89 (s,3H), 6.17 (s,1H), 6.86 (s,1H), 7.32 (s,1H); IR (KBr): 3680–2730, 3430, 3260, 1731, 1688, 1611, 1512, 1440, 1423 cm$^{-1}$; Elementary Analysis (for $C_{19}H_{20}O_8 \cdot 0.75H_2O$), Theory: C,58.53; H,5.56; Found: C,58.51; H,5.25.

EXAMPLE 3

3-Carboxy-4-methoxy-5-methylphenyl-(5'-carboxy-2',4'-dimethoxyphenyl) Ether

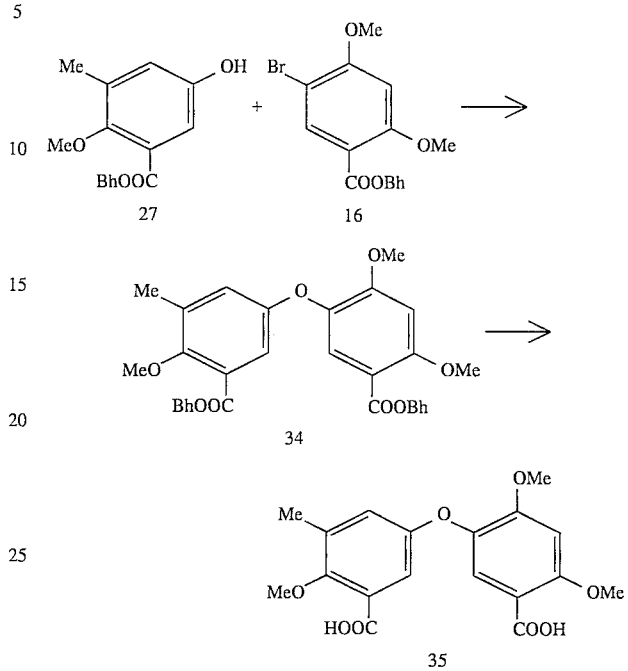

[Step 1] (27+16→34)

Compound 27 (1.0 g, 2.87 mM), and 16 (1.23 g, 2.87 mM) were treated in a similar procedure to that of Step 2 in Expample 1, to yield the crude compound 34. The compound was subjected to column chromatography (80 g of $SiO_2$, eluent: n-hexane—ethyl acetate (4:1) to (2:1)), to yield 400 mg of 34 as an oil (20%).

TLC (Rf: 0.1, Developer: n-hexane—ethyl acetate (4:1)); $^1$HNMR (CDCl$_3$): δ2.26 (s,3H), 3.67 (s,3H), 3.86 (s,3H), 3.96 (s,3H), 6.58 (s,1H), 6.87 (d,J=4 Hz,1H), 7.05 (s,1H), 7.07 (s,1H), 7.10–7.54 (m,11H), 7.70 (s,1H).
[Step 2] (34→35)

Compound 34 (320 mg, 461 μM) was treated in a similar procedure to that of Step 3 in Expample 1, to yield 112 mg of 35 as a pale yellow crystal (67%).

TLC (Rf: 0.3, Developer: ethyl acetate—acetic acid (1%)); $^1$HNMR (DMSO): δ2.22 (s,3H), 3.69 (s,3H), 3.86 (s,3H), 3.90 (s,3H), 6.82 (d,J=3.0 Hz,1H), 6.87 (s,1H), 6.95 (d,J=3.0 Hz,1H), 7.39 (s,1H); IR (KBr): 3680–2320, 3440, 2960, 1695, 1616, 1215, 1120 cm$^{-1}$; Elementary Analysis (for $C_{18}H_{18}O_8 \cdot 0.3H_2O$), Theory: C,58.79; H,5.10 (%); Found: C,58.86; H,5.09 (%).

EXAMPLE 4

Bis(3-carboxy-4,6-dimethoxy-2,5-dimethylphenyl) Methane

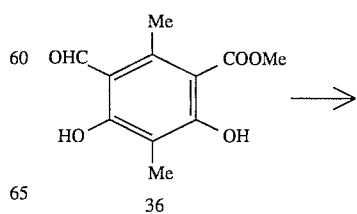

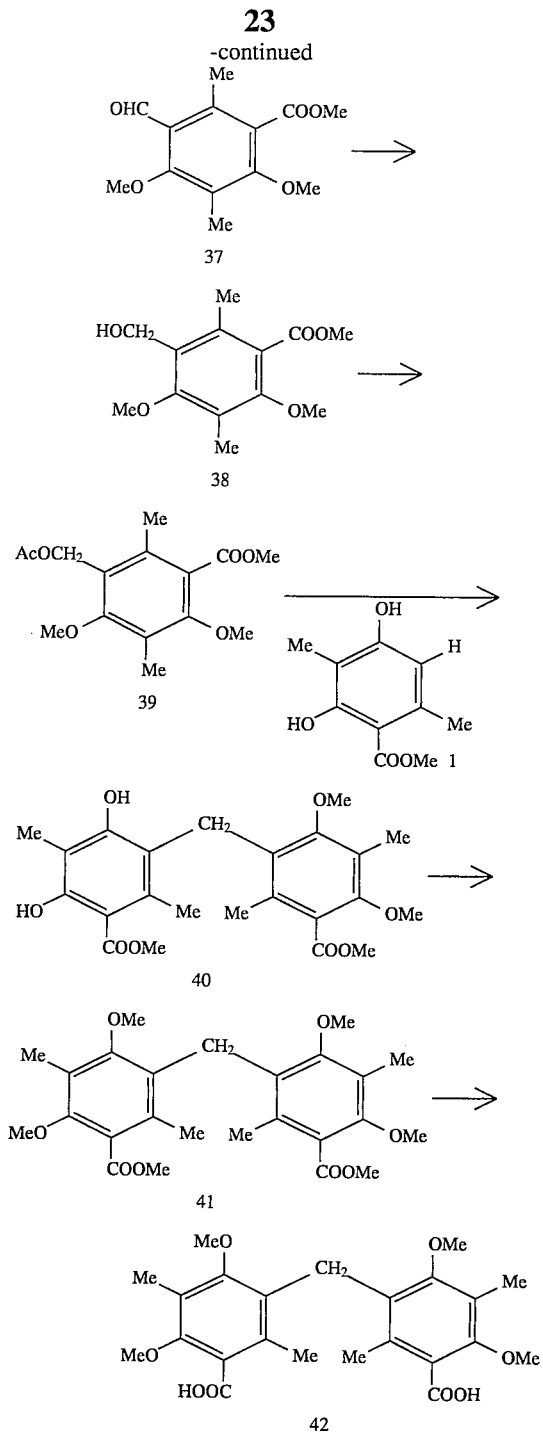

[Step 1] Synthsis of Acetate 39

The aldehyde 36 (3.70 g, 16.5 mM), which is described in the literature, was methoxylated by a similar procedure to that of Step 2 in Preparation 1, to yield 6.8 g of 37 as a red oil. The compound was dissolved in 30 ml of isopropyl alcohol, and to the solution was added NaBH$_4$ (0.94 g, 16.5 mM×1.5), and the reaction mixture was stirred, and then it was distributed between ethyl acetate and water. The organic phase was washed with 2N hydrochloric acid, followed by with water, dried, and then concentrated in vacuo. The resultant residue was subjected to column chromatography (70 g of SiO$_2$, eluent: n-hexane—ethyl acetate (4:1) to (1:1)), to yield 3.18 g of the alcohol 38 (76% based on 1).

Colorless oil. TLC (Rf: 0.2, Developer: n-hexane—ethyl acetate (4:1)).

Then, the oil was dissolved in 20 ml of CH$_2$Cl$_2$, and to the solution was added 6 ml of acetic anhydride, 10 ml of pyridine, and 50 mg of dimethylaminopyridine, and then the mixture was stirred at room temperature for two hours. The reaction mixture was distributed between ethyl acetate and 2N hydrochloric acid, and the organic phase was washed with water, and dried, then concentrated in vacuo to yield the crude compound 39. The compound was recrystallized from ether—n-hexane to yield 3.35 g of the acetate 39 (91%). Colorless piller crystals. M.p. 69°–70° C. TLC (Rf: 0.4, Developer: n-hexane—ethyl acetate (4:1)).

$^1$HNMR (CDCl$_3$): δ2.07 (s,3H), 2.22 (s,3H), 2.24 (s,3H), 3.74 (s,3H), 3.78 (s,3H), 3.93 (s,3H), 5.18 (s,2H).

[Step 2] Synthesis of 40

Compound 1 (1.45 g, 6.74 mM×1.1), which is known in the literature and the acetate 39 (2.00 g, 6.74 mM) were dissolved in 25 ml of toluene, and to the solution was added BF$_3$·OEt$_2$ (0.83 ml, 6.74 mM), and the mixture was stirred at room temperature for 15 minutes. To the reaction mixture was added ethyl acetate, then the mixture was washed with water, dried, and then concentrated in vacuo. The residue was subjected to column chromatography (SiO$_2$; Merck, Lobar B, eluent: n-hexane—ethyl acetate), to yield 2.91 g of 40 (100%). Colorless prism crystals. M.p. 169°–170° C. TLC (Rf: 0.3, Developer: n-hexane—ethyl acetate (4:1)).

$^1$HNMR (CDCl$_3$): δ2.07 (s,6H), 2.25 (s,3H), 2.55 (s,3H), 3.75 (s,6H), 3.88 (s,3H), 3.92 (s,3H), 3.95 (s,2H), 7.20 (s,1H), 11.38 (s,1H); IR (Nujol): 3285, 1743, 1644 cm$^{-1}$; Elementary Analysis (for C$_{23}$H$_{28}$O$_8$), Theory: C,63.87; H,6.54 (%); Found: C,63.65; H,6.57 (%).

[Step 3] Synthesis of 41

Compound 40 (2.91 g, 7.4 mM) was methoxylated in a similar procedure to that of Step 2 in Preparation 1, and the crude residue was subjected to column chromatography (60 g of SiO$_2$, eluent: toluene—ethyl acetate (9:1) to (4:1)), to yield 2.97 g of 41 (96%). Colorless pillar crystals. M.p. 271°–220° C. TLC (Rf: 0.5, Developer: benzene—ethyl acetate (9:1)).

$^1$HNMR (CDCl$_3$): δ2.03 (s,6H), 2.20 (s,6H), 3.48 (s,6H), 3.74 (s,6H), 3.88 (s,6H), 4.03 (s,2H); IR (Nujol): 1730, 1588, 1572, 1104 cm$^{-1}$; Elementary Analysis (for C$_{25}$H$_{32}$O$_8$), Theory: C,65.19; H,7.02 (%); Found: C,65.14; H,7.04 (%).

[Step 4] (41→42)

Compound 41 (600 mg, 130 mM) was hydrolyzed in a similar procedure to that of Step 3 in Preparation 1, to yield 559 mg of 42 as a colorless crystal (99%). M.p. 265°–267° C. TLC (Rf: 0.7, Developer: ethyl acetate—acetic acid—water (18:1:1)).

$^1$HNMR (DMSO): δ1.96 (s,6H), 2.12 (s,6H), 3.48 (s,6H), 3.66 (s,6H), 3.98 (s,2H); IR (KBr): 3670–2400, 3430, 2940, 1710, 1217, 1105 cm$^{-1}$, Elementary Analysis (for C$_{23}$H$_{28}$O$_8$·0.4H$_2$O), Theory: C,62.83; H,6.60 (%); Found: C,62.88; H,6.63 (%).

EXAMPLE 5

Bis[5-[4'-(4"-carboxy-3"-methoxy-2",5",6"-trimethylphenoxycarbonyl)-3'-methoxy-2',5',6'-trimethylphenoxycarbonyl]-2,4-dimethoxy-3,6-dimethylphenyl]methane

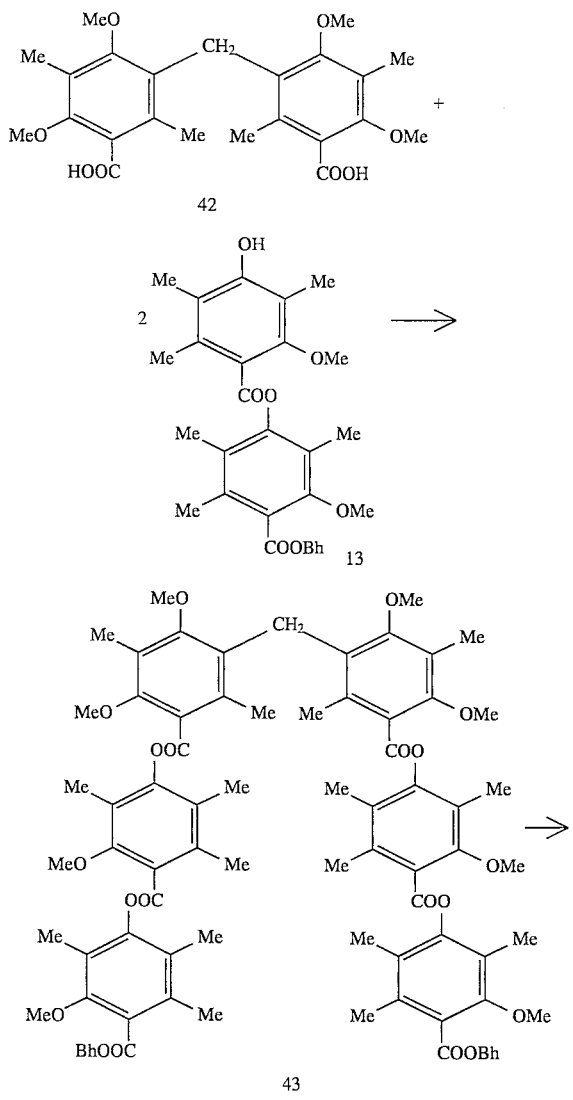

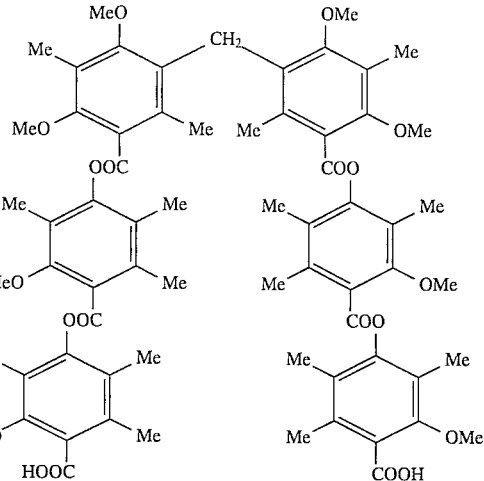

[Step 1] Synthesis of 43

Compound 42 (100 mg, 231 μM) and 13 (263 mg, 231 μM×2) were esterified in a similar procedure to that of Step 4 in Preparation 2, to yield the crude compound 43. The compound was subjected to column chromatography (15 g of $SiO_2$, eluent: n-hexane—ethyl acetate (4:1) to (2:1)), to yield 219 mg of 43 as a colorless crystal (62%). M.p. 245°–247° C. TLC (Rf: 0.7, Developer: benzene—ethyl acetate (9:1)).

$^1$HNMR (CDCl$_3$): δ2.08 (s,6H), 2.20 (s,6H), 2.25 (s,12H), 2.30 (s,18H), 2.39 (s,6H), 3.57 (s,6H), 3.60 (s,6H), 3.83 (s,12H), 4.17 (s,2H), 7.19 (s,2H), 7.22–7.50 (m,20H); IR (Nujol): 1745, 1150, 1097, 1074 cm$^{-1}$; Elementary Analysis (for C$_{93}$H$_{96}$O$_{20}$), Theory: C,72.83; H,6.31 (%); Found: C,72.74; H,6.33 (%).

[Step 2] Synthesis of 44

Compound 43 (186 mg, 121 μM) was deprotected in a similar procedure to that of Step 3 in Example 1, to yield mg of 44. as a colorless powder (96%). TLC (Rf: 0.4, Developer: ethyl acetate—acetic acid (1%)).

$^1$HNMR (DMSO): δ2.12–2.40 (m,48H), 3.54 (s,6H), 3.73 (s,6H), 3.77 (s,12H), 4.14 (s,2H); IR (KBr): 3680–2400, 3450, 2940, 1743, 1697, 1140 cm$^{-1}$; Elementary Analysis (for C$_{67}$H$_{76}$O$_{20}$), Theory: C,66.99; H,6.38 (%); Found: C,66.73; H,6.31 (%).

EXAMPLE 6–11
The following compounds were synthesized as shown above.
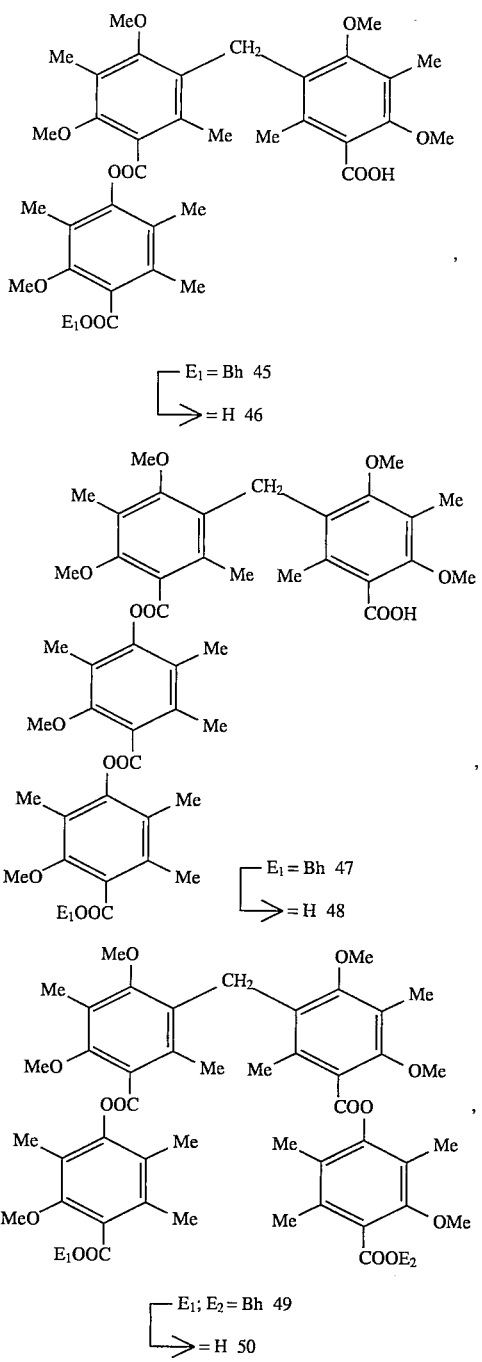
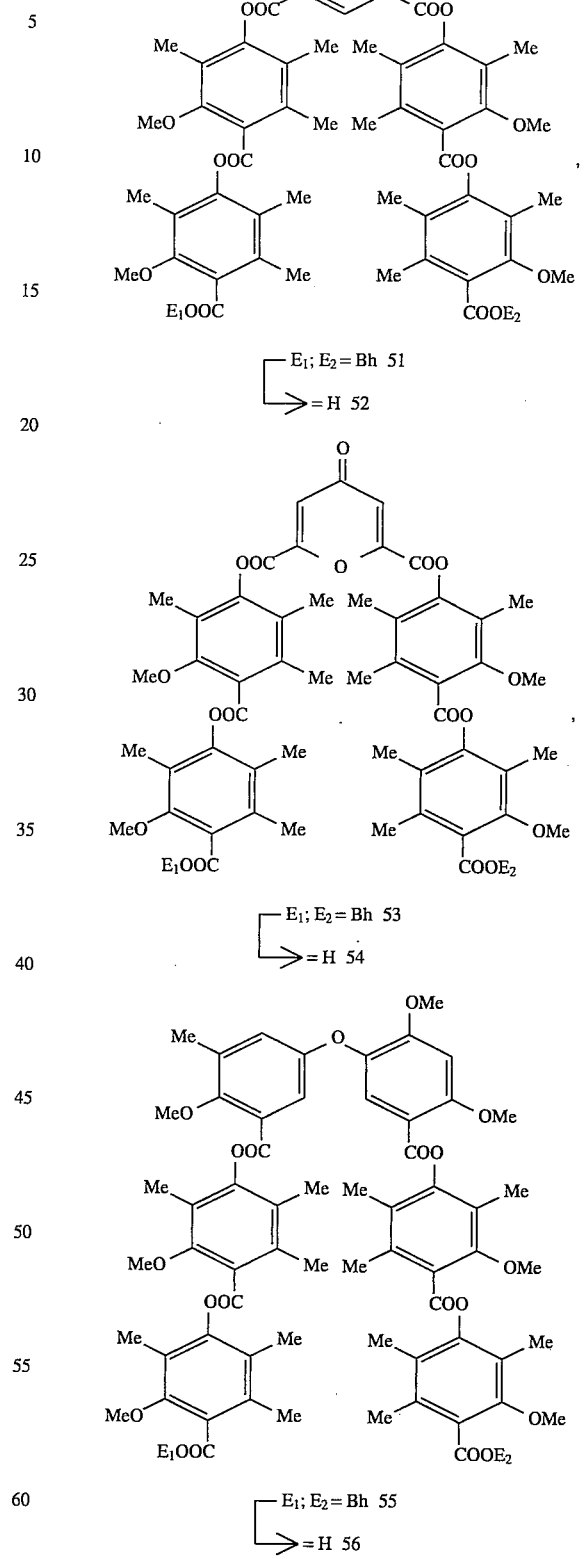

| Example | Compound | Starting Material COOH | Starting Material OH | Ratio (COOH:OH) | yield |
|---------|----------|------------------------|----------------------|-----------------|-------|
| 6 | 46 | 42 | 10 | 1:1 | 17% |
| 7 | 48 | 42 | 13 | 1:1 | 20% |
| 8 | 50 | 42 | 10 | 1:2 | 70% |
| 9 | 52 | isophthalic acid | 13 | 1:2 | 60% |
| 10 | 54 | chelidonic acid | 13 | 1:2 | 27% |
| 11 | 56 | 35 | 13 | 1:2 | 42% |

Physicochemical Data

Compound 46; Colorless crystals. M.p. 141°–143° C. TLC (Rf: 0.4, Developer: ethyl acetate—acetic acid (1%)).

$^1$HNMR (CD$_3$OD): δ1.99 (s,3H), 2.10 (s,3H), 2.16–2.28 (m,15H), 3.54 (s,3H), 3.62 (s,3H), 3.77 (s,3H), 3.78 (s,3H), 3.80 (s,3H), 4.16 (s,2H); IR (KBr): 3420, 2930, 1738, 1569, 1150, 1095 cm$^{-1}$.

Compound 48; Colorless powder. TLC (Rf: 0.4, Developer: ethyl acetate—acetic acid (1%)).

$^1$HNMR (CD$_3$OD): δ2.00 (s,3H), 2.11 (s,3H), 2.18–2.34 (m,21H), 2.41 (s,3H), 3.57 (s,3H), 3.63 (s,3H), 3.77 (s,3H), 3.82 (s,3H), 3.83 (s,3H), 4.18 (s,2H); IR (KBr): 3440, 2950, 1745, 1703, 1570, 1460, 1145, 1095, 1075 cm$^{-1}$.

Compound 50; Colorless crystals. M.p. 267°–269° C. TLC (Rf: 0.4, Developer: ethyl acetate—acetic acid (1%)).

$^1$HNMR (DMSO): δ2.04–2.28 (m,30H), 3.52 (s,6H), 3.70 (s,6H), 3.74 (s,6H), 4.11 (s,2H); IR (KBr): 3440, 2940, 1740, 1700, 1460, 1155 cm$^{-1}$; Elementary Analysis (for C$_{45}$H$_{52}$O$_{14}$), Theory: C,66.16; H,6.42 (%); Found: C,65.97; H,6.48 (%).

Compound 52; Colorless crystals. M.p. 267°–269° C. TLC (Rf: 0.4, Developer: ethyl acetate—acetic acid (1%)).

$^1$HNMR (DMSO): δ2.08–2.26 (m,30H), 2.37 (s,6H), 3.73 (s,6H), 3.79 (s,6H), 7.98 (t,J=9 Hz,1H), 8.66 (dd, J=9 Hz, J=1Hz,2H ), 8.93 (m,1H); IR (KBr): 3430, 2940, 1745, 1700, 1222, 1160 cm$^{-1}$; Elementary Analysis (for C$_{52}$H$_{54}$O$_{16}$.H$_2$O), Theory: C,65.54; H,5.92 (%); Found: C,65.44; H,5.84 (%).

Compound 54; Colorless plate crystals. M.p. 294°–296° C. TLC (Rf: 0.3, Developer: ethyl acetate—acetic acid (1%)).

$^1$HNMR (CDCl$_3$): δ2.16 (s,6H), 2.21 (s,6H), 2.26 (s,6H), 2.29 (s,6H), 2.36 (s,6H), 2.42 (s,6H), 3.84 (s,6H), 3.87 (s,6H), 7.52 (s,2H); Elementary Analysis (for C$_{51}$H$_{52}$O$_{18}$), Theory: C,64.27; H,5.51 (%); Found: C,63.88; H,5.57 (%).

Compound 56; Colorless powder (hygroscopic). TLC (Rf: 0.3, Developer: ethyl acetate—acetic acid (1%)).

$^1$HNMR (DMSO): δ1.90 (s,3H), 1.98–2.90 (m,27H), 2.28–2.37 (m,9H), 3.68–3.81 (m,15H), 3.96 (s,3H), 4.00 (s,3H), 7.03 (s,1H), 7.18 (d,J=2.8 Hz,1H), 7.28 (d,J=2.8 Hz,1H), 7.80 (s,1H); IR (KBr): 3430, 2930, 1745, 1575, 1462, 1150 cm$^{-1}$; Elementary Analysis (for C$_{62}$H$_{66}$O$_{20}$.3.5H$_2$O), Theory: C, 62.36; H,6.16 (%); Found : C, 62.31; H,5.92 (%).

EXAMPLE 12 n-Butyl 3-[3'-(4''-Carboxy-3''-methoxy-2'',5'',6''-trimethylphenoxycarbonyl)-4'-methoxyphenyl]-thio-6-methoxybenzoate

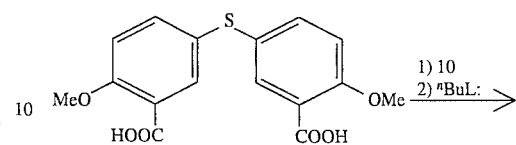

57

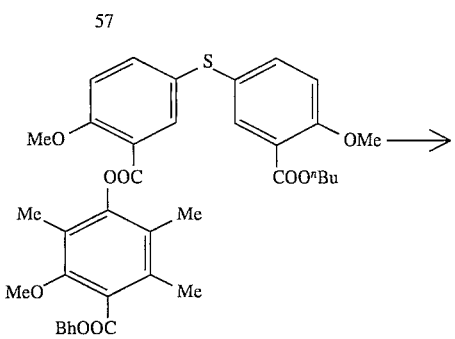

58

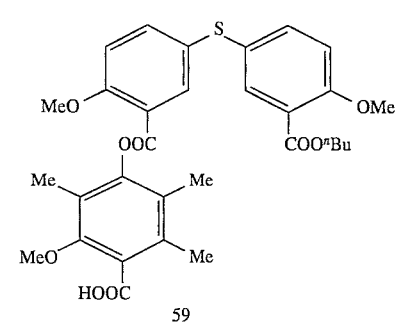

59

Synthesis of 59

Compound 57 (50 mg, 150 μM) and 10 (56 mg, 150 μM) were treated in a similar procedure to that of Step 4 in Preparation 2, to yield the half-ester. The compound was reacted with n-butyl lithium (1.6N solution in hexane, μl, 150 μM), and the reaction mixture was worked up in a conventional manner to yield the crude compound 58. The compound was subjected to column chromatography (3 g of SiO$_2$, eluent: toluene—ethyl acetate (1:0) to (4:1)), to yield 58 as a colorless oil. The oil was deprotected in a similar procedure to that of Step 3 in Example 1 to yield 14 mg of 59 (16%). Colorless oil.

TLC (Rf: 0.5, Developer: ethyl acetate—acetic acid 1%));
$^1$HNMR (CDCl$_3$): δ0.95 (t,J=7.2 Hz,3H), 1.30–1.53 (m,2H), 1.59–1.80 (m,2H), 2.08 (s,3H), 2.09 (s,3H), 2.30 (s,3H), 3.80 (s,3H), 3.89 (s,3H), 3.92 (s,3H), 4.27 (t,J=7 Hz,2H), 6.90–7.05 (m,2H), 7.40–7.54 (m,2H), 7.82 (d,J=1.2 Hz,1H), 8.01 (J=1.2 Hz,1H).

EXAMPLE 13

Bis[5-[4'-(4''-pivaloyloxymethyloxycarbonyl-3''-methoxy-2'',5'',6''-trimethylphenoxycarbonyl)-3'-methoxy-2',5',6'-trimethylphenoxycarbonyl]-2,4-dimethoxy-3,6-dimethylphenyl] Methane 44 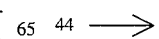

-continued

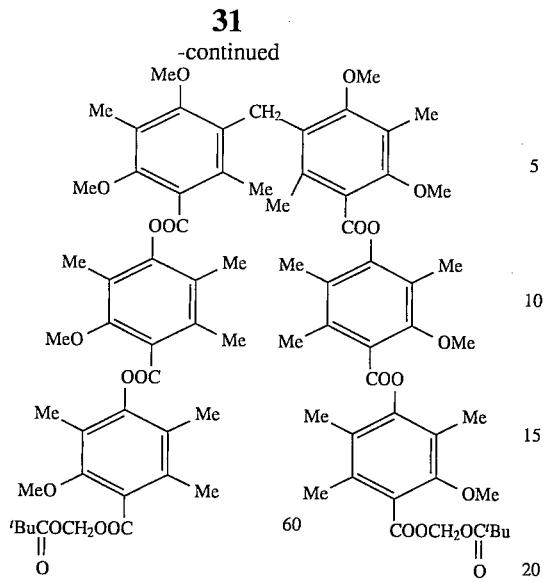

60

Synthesis of 60

Compound 44 (100 mg, 83.2 μM) was dissolved in acetone (1 ml), and to the solution was added pivaloyloxymethyl iodide (tBuCOOCH$_2$I: 48 mg, 83.2 μM×2.4) dissolved in 3 ml of acetone and then anhydrous K$_2$CO$_3$ (40 mg, 83.2 μM×3.5) was added thereto, and the resultant mixture was stirred at room temperature for two and a half days. The reaction mixture was worked up in a conventional manner, and then it was subjected to column chromatography (10 g of SiO$_2$, eluent: toluene—ethyl acetate (19:1) to (9:1)), and the residue was crystallized from ether—n-hexane, to yield 103 mg of 60 as a colorless crystal (87%). M.p. 211°–213° C. TLC (Rf: 0.3, Developer: benzene—ethyl acetate (9:1)).

$^1$HNMR (CDCl$_3$): δ1.28 (s,18H), 2.20–2.37 (m,42H), 2.41 (s,6H), 3.62 (s,6H), 3.74–3.88 (m,18H), 4.27 (s,2H), 6.01 (s,4H); IR (Nujol): 1751, 1570, 1150, 983 cm$^{-1}$; Elementary Analysis (for C$_{79}$H$_{96}$O$_{24}$·H$_2$O), Theory: C,65.55; H,6.82 (%); Found: C,65.58; H,6.63 (%).

EXAMPLE 14

Bis[5-[4'-(4"-carboxy-3"-hydroxy-2',5",6"-trimethylphenoxycarbonyl)-3'-hydroxy-2',5',6'-trimethylphenoxycarbonyl]-2,4-dihydroxy-3,6-dimethylphenyl] Methane

43 →

-continued

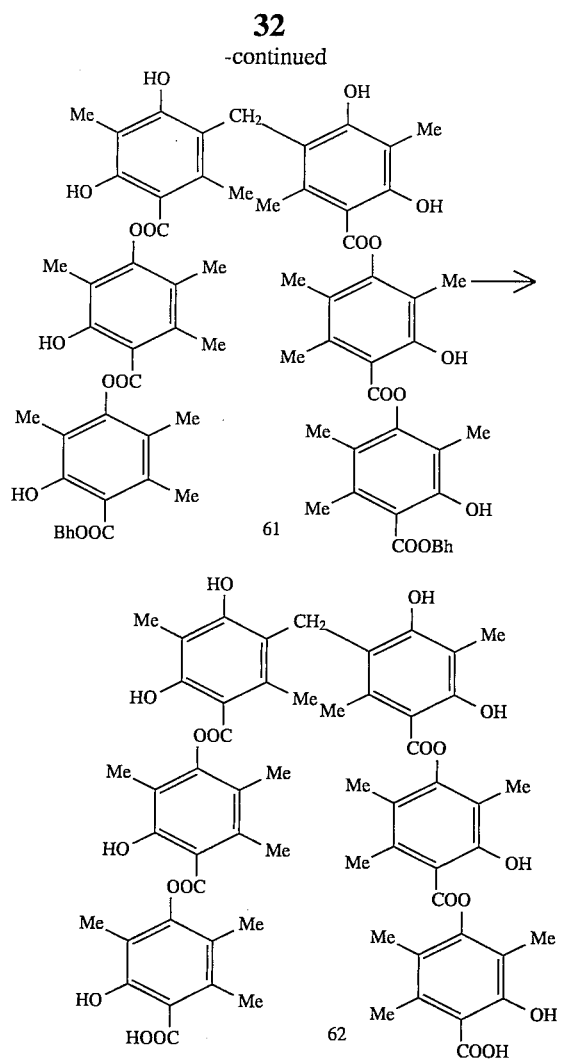

61

62

[Step 1] 43→61

A mixture containing the compound 43 (500 mg, 326 μM), BBr$_3$ (371 μl, 326 μM×12), and CH$_2$Cl$_2$ (15 ml) was stirred at room temperature for 6 hours, and water was added thereto, and then the resultant mixture was distributed between ethyl acetate and brine. The organic phase was washed with brine three times, dried, and concentrated in vacuo. The residue was dissolved in ethyl acetate (6 ml), and the solution was subjected to benzhydrylation in a similar procedure to that of Step 5 in Preparation 1, to yield the crude compound 61. The compound was subjected to column chromatography (Lober (Merck: B), eluent: toluene—ethyl acetate (1:0) to (0:1)), and the residue was powdered in ethyl—n-hexane to yield 162 mg of 61 as a colorless powder (35%). TLC (Rf: 0.5, Developer: benzene—ethyl acetate (9:1)).

$^1$HNMR (CDCl$_3$): δ2.00–2.20 (m,30H), 2.55 (s,6H), 2.67 (s,6H), 2.74 (s,6H), 4.17 (s,2H), 6.31 (s,2H), 7.20 (s,2H), 7.28–7.48 (m,20H), 11.04 (s,2H), 11.33 (s,2H), 11.56 (s,2H).

[Step 2] 61→62

Compound 61 (61 mg, 106 μM) was subjected to hydrogenation in a similar procedure to that of Step 4 in Preparation 1, to yield 62. The compound was crystallized from ether to yield 49 mg of 62 as a colorless crystal (43%). M.p. (dec.); 162°–220° C. TLC (Rf: 0.2, Developer: ethyl acetate—acetic acid (1%)).
$^1$HNMR (DMSO): δ1.96–2.40 (m,48H), 4.09 (s,2H), 9.43 (s,2H), 9.90 (s,2H); IR(Nujol): 3700–2560, 1670, 1455, 1155 cm$^{-1}$.
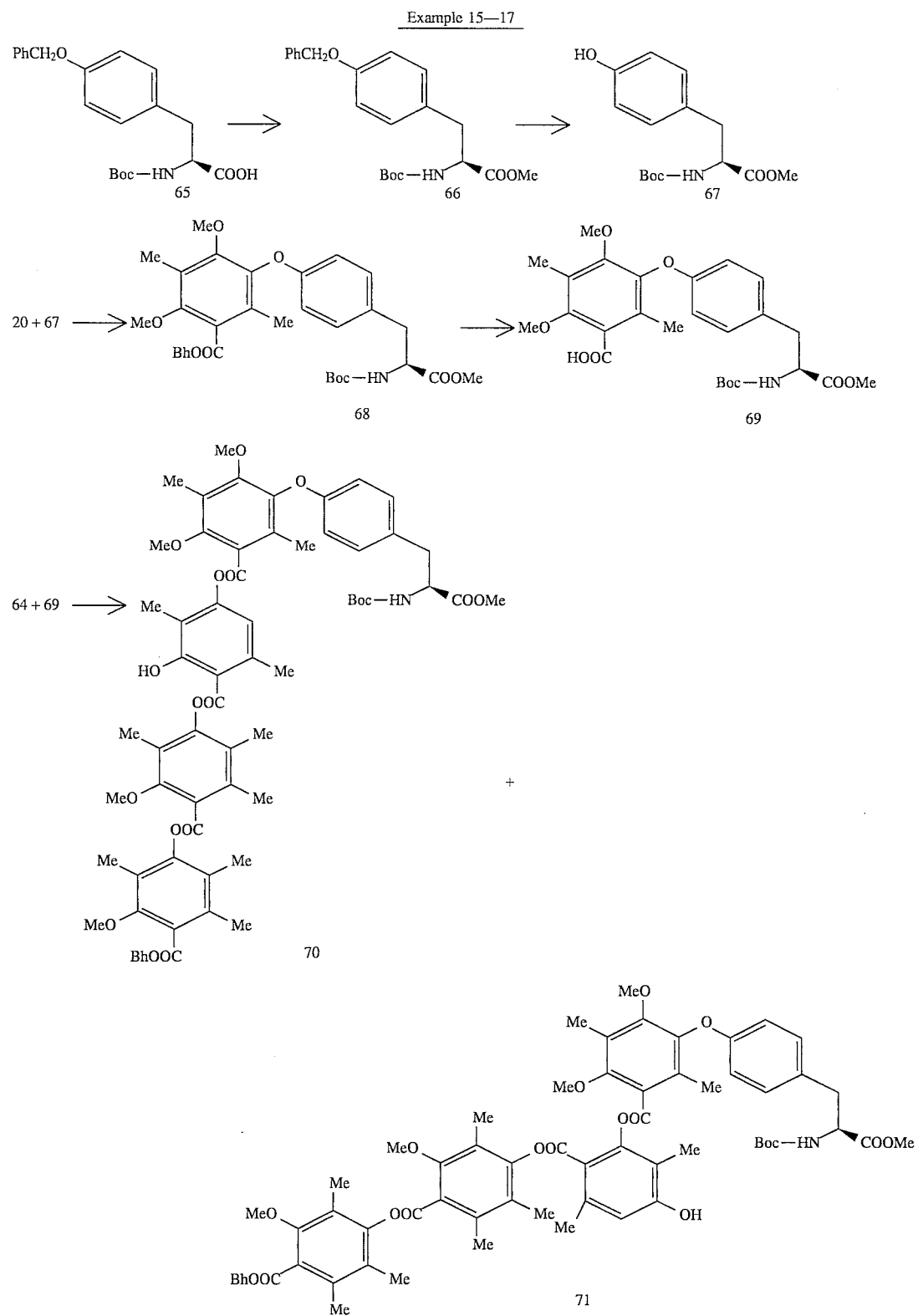
Example 15—17

[Step 1] Synthesis of the Compound 67

Diazomethane gas was generated by stirring a solution of N-methyl nitrosourea (10 g, 20.2 mM×4.8) in ether and an aqueous solution of potassium hydroxide, and the gas was trapped into an ice-cooling ether, to make a solution of diazomethane in ether. Then, the ether solution was added to a methanol solution of N-t-Boc-O-benzyl-L-tyrosine 65 (7.5 g, 20.2 mM), until the solution developed yellow. Acetic acid was added thereto until the solution became colorless in order to decompose excess diazomethane. The material was concentrated in vacuo to yield 66. The compound was dissolved in methanol, and it was subjected to hydrogenation in a similar procedure to that of Step 4 in Preparation 1, to yield the crude compound 67. The compound was recrystallized from ether—n-hexane to yield 5.88 g of 67 as a colorless crystal (99%). M.p. 100°–101° C. TLC (Rf: 0.3, Developer: benzene—ethyl acetate (4:1)).

$^1$HNMR (CDCl$_3$): δ1.42 (s,9H), 2.94–3.06 (m,2H), 3.72 (s,3H), 4.26–4.61 (m, 1H), 4.92–5.06 (m,1H), 5.42 (s,1H), 6.74 (d,J=8.2 Hz,2H), 6.98 (d,J=8.2 Hz,2H); IR (Nujol): 3399, 1716, 1690, 1519 cm$^{-1}$; $[α]^{25.0}_D$=+49.1°±0.9° (CHCl$_3$, C=1.008%); Elementary Analysis (for C$_{15}$H$_{21}$NO$_5$·0.4H$_2$O), Theory: C,59.55; H,7.26;N,4.63 (%); Found: C,59.55; H,6.88;N,4.71 (%).

[Step 2] 20+67→68

Compound 20 (2.56 g, 5.61 mM) and 67 (1.66 g, 5.61 mM) were treated in a similar procedure to that of Step 2 in Example 1, to yield the crude compound 68. The compound was subjected to column chromatography (75 g of SiO$_2$, eluent: n-hexane—ethyl acetate (9:1) to (4:1)), to yield 226 mg of 6.8 (6%). Colorless foam. TLC (Rf: 0.2, Developer: n-hexane—ethyl acetate (2:1)).

$^1$HNMR (CDCl$_3$): δ1.41 (s,9H), 1.95 (s,3H), 2.18 (s,3H), 2.94–3.04 (m,2H), 3.58 (s,3H), 3.70 (s,3H), 3.71 (s,3H), 4.24–4.62 (m, 1H), 4.89–5.01 (m, 1H), 6.72 (d,J=8.4 Hz,2H), 7.00 (d,J=8.4 Hz,2H), 7.17 (s,1H), 7.26–7.48 (m,10H); IR (Nujol): 3370, 1720, 1169 cm$^{-1}$; $[α]^{24.0}_D$=+24.1°±0.6° (CHCl$_3$, C=1.002%); Elementary Analysis (for C$_{39}$H$_{43}$NO$_9$), Theory: C,69.94; H,6.47;N,2.09 (%); Found: C,69.85; H,6.44;N,2.17 (%).

[Step 3] 68→69

Compound 68 (198 mg, 296 μM) was subjected to hydrogenation in a similar procedure to that of Step 4 in Preparation 1, to yield 149 mg of 69 (100%). Colorless foam. TLC ( Rf: 0.1, Developer: benzene—ethyl acetate (4:1)).

$^1$HNMR (CDCl$_3$): δ1.41 (s,9H), 2.22 (s,3H), 2.23 (s,3H), 2.94–3.09 (m,2H), 3.71 (s,3H), 3.76 (s,3H), 3.86 (s,3H), 4.48–4.64 (m,1H), 4.94–5.06 (m, 1H), 6.72 (d,J=8.6 Hz,2H), 7.02 (d,J=8.6 Hz,2H).

[Step 4] 64+69→70+71

Compound 64 (434 mg, 296 μM×2) and 69 (149 mg, 296 μM) were treated in a similar procedure to that of Step 4 in Preparation 2, to yield the mixutre comprising 70 and 71. The mixture was subjected to column chromatography (15 g of SiO$_2$, eluent: toluene—ethyl acetate (2%) to (28%)), to yield 70 (145 mg, 40%) and 71 (118 mg, 33%).

Compound 70: Colorless glassy material. TLC (Rf: 0.5, Developer: benzene—ethyl acetate (9:1)).

$^1$HNMR (CDCl$_3$): δ1.42 (s,9H), 2.05–2.45 (m,27H), 2.76 (s,3H), 3.57 (s,3H), 3.72 (s,3H), 3.78 (s,3H), 3.84 (s,3H), 3.91 (s,3H), 4.52–4.64 (m,1H), 4.93–5.05 (m, 1H), 6.70 (s,1H), 6.78 (d,J=8.6 Hz,2H), 7.05 (d,J=8.6 Hz,2H), 7.20 (s,1H), 7.25–7.50 (m,10H), 11.81 (s,1H).

Compound 71: Colorless glassy material. TLC (Rf: 0.1, Developer: benzene—ethyl acetate (9:1)).

$^1$HNMR (CDCl$_3$): δ1.90–2.38 (m,27H), 2.50 (s,3H), 2.88–3.01 (m,2H), 3.57 (s,3H), 3.65 (s,3H), 3.73 (s,3H), 3.74 (s,3H), 3.86 (s,3H), 4.46–4.58 (m, 1H), 4.90–5.02 (m, 1H), 5.71 (s,1H), 6.61 (d,J=8.4 Hz,2H), 6.70 (s,1H), 6.98 (d,J=8.4 Hz,2H), 7.20 (s,1H), 7.28–7.50 (m,10H).

EXAMPLE 18

[5-[4'-[4''-(4'''-Carboxy-3'''-methoxy-2''',5''',6'''-trimethylphenoxycarbony)-3''-methoxy-2'',5'',6''-trimethylphenoxycarbony]-3'-hydroxy-2',5'-dimethylphenoxycarbony]-2,4-dimethoxy-3,6-dimethylphenyl][4''''-(2'''''-amino-2'''''-carboxyethyl)phenyl]ether Trifluoroacetate

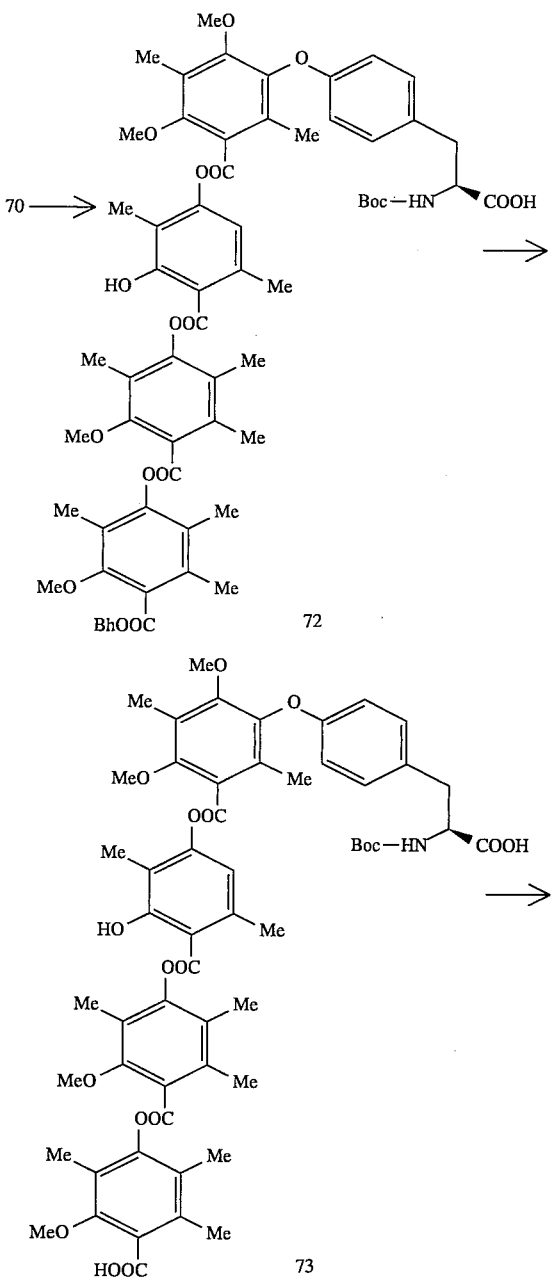

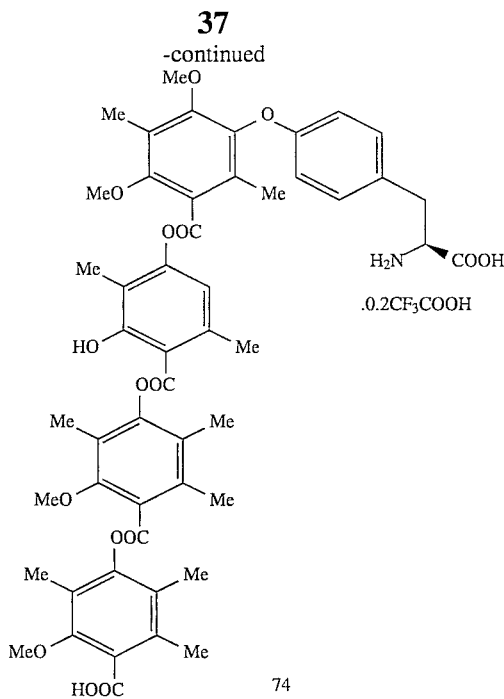

[Step 1] 70→73

Compound 70 (128 mg, 105 μM) was hydrolyzed in a similar procedure to that of Step 3 in Preparation 1, to yield 122 mg of 72 (96%). Colorless oil. TLC (Rf: 0.4, Developer: ethyl acetate—acetic acid (1%)). The compound was subjected to hydrogenation in a similar procedure to that of Step 4 in Preparation 1, to yield 105 mg of 73 (100%). Colorless powder. TLC (Rf: 0.3, Developer: ethyl acetate—acetic acid (1%)).

$^1$HNMR (CDCl$_3$): δ2.10–2.46 (m,27H), 2.76 (s,3H), 3.03–3.08 (m,2H), 3.74–3.92 (m,12H), 4.52–4.68 (m,1H), 4.92–5.02 (m,1H), 6.70 (s,1H), 6.80 (d,J=8.6 Hz,2H), 7.13 (d,J=8.6 Hz,2H), 11.80 (s,1H).

[Step 2] 73→74

A mixuture containing 73 (109 mg, 105 μM), trifluoroacetic acid (1.2 ml), and methylene chloride (2 ml) was stirred at room temperature for two hours, and the resultant mixture was directly concentrated in vacuo. The residue was dissolved in ethyl acetate, and the solution was again concentrated in vacuo. The residue was powdered in ethyl acetate—ether to yield 64 mg of 74 (58%). Colorless powder. $^1$HNMR (DMSO): δ2.10–2.58 (m,30H), 2.72–2.92 (m,2H), 3.73 (m,6H), 3.78 (s,3H), 3.84 (s,3H), 6.74 (d,J=8.6 Hz,2H), 6.80 (s,1H), 7.22 (d,J=8.6 Hz,2H); IR (Nujol): 3680–2280, 1750, 1700, 1665, 1610, 1160, 1140, 1080 cm$^{-1}$; [α]$^{26.0}_D$=−12.1°±0.8° (DMSO, C=0.644%); Elementary Analysis (for C$_{51}$H$_{55}$NO$_{16}$.0.2CF$_3$COOH), Theory: C,64.26; H,5.79;N,1.49; F,1.19 (%); Found : C,64.18; H,5.89;N,1.49; F,0.95 (%).

EXAMPLE 19

[5-[6'-[4''-(4'''-Carboxy-3'''-methoxy-2''',5''',6'''-trimethylphenoxycarbonyl-3''-methoxy-2'',5'',6''-trimethylphenoxycarbony]-3'-hydroxy-2',5'-dimethylphenoxycarbony]-2,4-dimethoxy-3,6-dimethylphenyl][4''''-(2'''''-amino-2'''''-carboxyethyl)phenyl]ether Trifluoroacetate

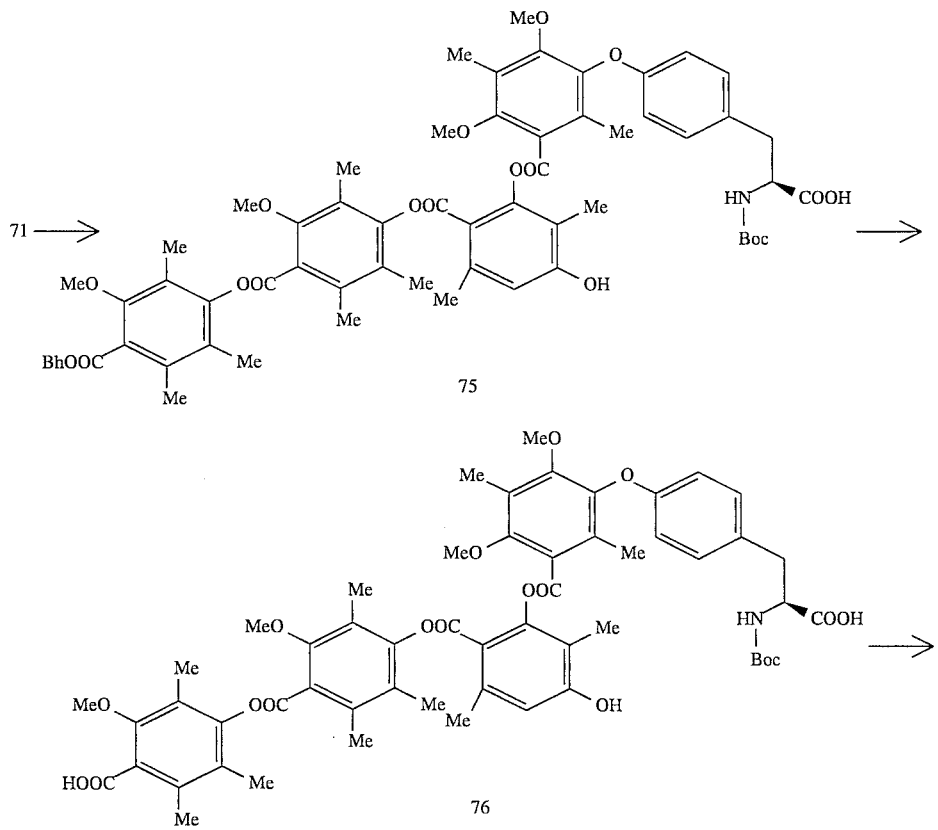

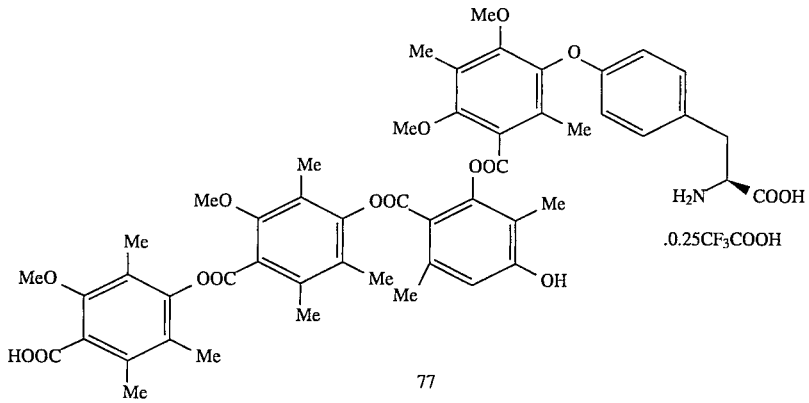

77

[Step 1] 71→75

Compound 71 (110 mg, 90.3 μM) was hydrolyzed in a similar procedure to that of Step 3 in Preparation 1, to yield 100 mg of 7.5 (92%). Colorless oil. TLC (Rf: 0.5, Developer: ethyl acetate—acetic acid (1%)).

¹HNMR (CDCl₃): δ1.90–2.50 (m,30H), 2.78–3.02 (m,2H), 3.56 (s,3H), 3.73 (s,3H), 3.74 (s,3H), 3.87 (s,3H), 4.40–4.54 (m, 1H), 4.90–5.00 (m,1H), 6.56 (d,J=8.6 Hz,2H), 6.68 (s,1H), 7.00 (d,J=8.6 Hz,2H), 7.21 (s,1H), 7.28–7.50 (m,10H).

[Step 2] 75→76

Compound 75 (100 mg, 83.0 μM) was subjected to hydrogenation in a similar procedure to that of Step 4 in Preparation 1, to yield 70 mg of 76 (81%). Colorless powder. TLC (Rf: 0.3, Developer: ethyl acetate—acetic acid (1%)).

¹HNMR (d₆-acetone): δ1.33 (s,9H), 1.92–2.05 (m,9H), 2.18–2.40 (m,18H), 2.49 (s,3H), 2.97–3.17 (m,2H ), 3.75 (s,3H), 3.78 (s,3H), 3.81 (s,3H ), 3.93 (s,3H), 4.24–4.46 (m,1H), 5.91–6.02 (m, 1H), 6.63 (d,J=8.6 Hz,2H), 6.88 (s,1H ), 7.18 (d,J=8.6 Hz,2H), 7.25 (s,1H); IR (Nujol): 3680–2260, 3340, 1730, 1158 cm⁻¹.

[Step 3] 76–77

Compound 76 (70 mg, 67.4 μM) was deprotected in a similar procedure to that of Step 2 in Example 18, to yield mg of 77 (73%). Colorless and hygroscopic powder. (Rf: 0.5, Developer: ethyl acetate—acetic acid—water (8:1:1)).

IR (Nujol): 3690–2400, 3400, 1735, 1276, 1158 cm⁻¹; [α]²⁶·⁰_D=−9.3°±1.0° (DMSO, C=0.515%); Elementary Analysis (for C₅₁H₅₅NO₁₆·0.25CF₃COOH·3.5H₂O), Theory: C,60.77; H,5.99;N,1.34; F,1.36 (%); Found: C,60.85; H,5.80;N,1.55; F,1.42 (%).

EXAMPLE 20

Bis[3-[4'-[(4"-carboxy-3"-methoxy, 2",5",6"-trimethyl)phenoxycarbony]-3'-methoxy,2',5',6'-trimethyl]-phenoxycarbony-4-methoxyphenyl] Sulfide

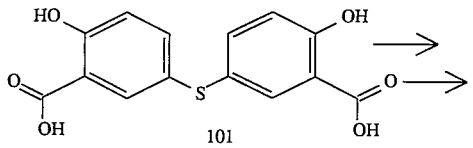

101

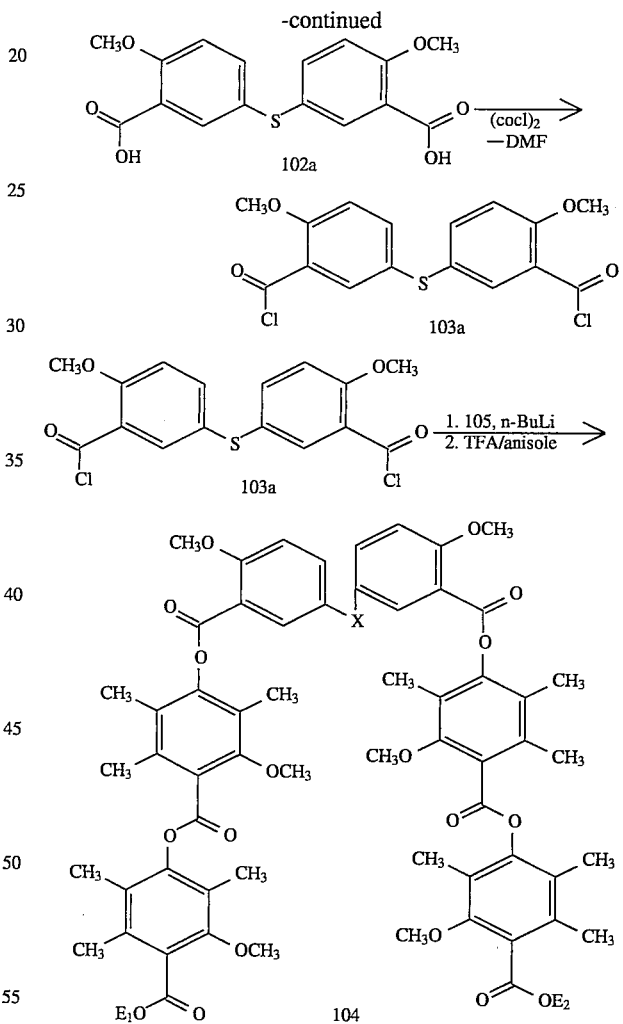

104a: X = S, E₁, E₂ = H
104b: X = SO₂, E₁, E₂ = H
104c: X = SO, E₁, E₂ = H
104d: X = S, E₁, E₂ = PCM

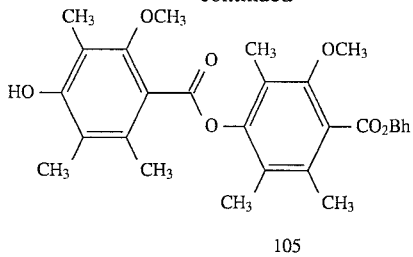

105

[Step 1]

5,5'-Thio-disalicylic acid (6.62 g, 0.022 mol) was dissolved in 300 ml of acetone, and 11.0 g of MeSO$_4$ (0.087 mol) and 15.2 g of K$_2$CO$_3$ (0.11 mol) were added thereto, and then the mixture was heated under reflux with stirring for seven hours. After cooling, 400 ml of ice-water was added to the mixture. Then, the resultant mixture was extracted with chloroform (200 ml×2), and the organic phase was dried (Na$_2$SO$_4$), and then evaporated to dryness in vacuo, to yield 8.22 g of the residue as an oil.

The oil (8.22 g), which was the crude dimethyl ester, was dissolved in 300 ml of methanol, and 50 ml of 1 M KOH solution in water was added thereto, and then the mixture was heated under reflux for three hours. The mixture was cooled to room temperature, and then the mixture was neutralized by adding 3.3 g of acetic acid thereto. The resultant mixuture was evaporated to dryness in vacuo, and the residue was distributed between chloroform and water. The organic phase was washed with water, dried (Na$_2$SO$_4$), and then concentrated in vacuo to yield 7.7 g of the solid. The solid was washed with a small amount of ether to yield 5.78 g of 102a (76%). M.p. 158°–159° C. (chlorform—n-hexane).

Elementary Analysis (for C$_{16}$H$_{14}$O$_6$S), Theory (%): C;57.34, H;4.15, S;9.39; Found (%): C;57.47, H;4.22, S;9.59.

[Step 2]

The compound 102a (58.7 mg, 0.18 mmol) obtained above were dissolved in 2 ml of anhydrous methylene chloride, and to the solution was added 0.16 ml of oxalyl chloride (1.8 mmol) dropwise at room temperature, followed by adding two drops of 10% solution of dimethylformamide in methylene chloride. The mixture was stirred at room temperature for one hour, and then 40°–50° C. (temperature of oil bath) for additional one hour.

The reaction mixture was evaporated to dryness in vacuo, and the residue was dissolved in 4 ml of anhydrous tetrahydrofuran, and the solution was evaporated to dryness in vacuo. The remaining excess of the reagents was removed by repeating the procedure twice, and then the residue was dissolved in 3 ml of tetrahydrofuran to yield a solution of 103a in tetrahydrofuran.

Compound 105 (200 mg, 0.35 mmol) was dissolved in 5 ml of tetrahydrofuran, and 0.23 ml of a 1.55M solution of n-butyl lithium in n-hexane was added slowly thereto dropwise at −78° C., and then the mixture was stirred at −78° C. for one hour. Then, to the solution was added slowly the solution of 103a in tetrahydrofuran obtained above dropwise at −78° C., and the mixture was stirred at −78° C. for 30 minutes. The reaction mixture was allowed to warm to the room temperature with stirring over 1.5 hours. The mixture was evaporated to dryness in vacuo, and the residue was distributed between 1N hydrochloric acid and ethyl acetate, and the organic phase was washed with an aqueous saturated sodium bicarbonate solution and a saturated brine, dried (Na$_2$SO$_4$), and then concentrated in vacuo to yield 0.28 g of the colorless oil. The oil was purified by preparative thin layer chromatography (KGF (Merck), Developer: ethyl acetate:n-hexane=1:2) to yield 138 mg of the benzhydryl ester of 104a (54.7%).

NMR (CDCl$_3$): 2.08, 2.13, 2.17, 2.20, 2.25, 2.38 (CH$_3$, each s), 3.57, 3.81, 3.96 (OCH$_3$, each s), 7.02–8.09 (aromatic H, multiplet).

Dibenzhydrol ester of 104a (138 mg, 0.1 mmol) was dissolved in 5 ml of methylene chloride, and the solution was cooled to 0° C., and a solution of anisole (46 mg, 0.43 mmol) and trifluoroacetic acid (110 mg) in 1 ml of methylene chloride was added to the solution. After the resultant solution was stirred at 0° C. for five hours, the reaction mixture was allowed to warm to the room temperature, and evaporated to dryness to yield 181 mg of the colored sticky oil. The oil was purified by preparative thin layer chromatograph (KGF (Merck), Developer: chloroform—methanol= 3:1) to yield 68 mg of 104a (64%). M.p. 278°–280° C. (dec.) (recrystallized from aqueous ethanol).

Elementary Analysis (for C$_{60}$H$_{62}$O$_{18}$S.½H$_2$O), Theory (%): C;64.96, H;5.76, S;2.79; Found (%): C;64.80, H;5.71, S;2.88; NMR (CDCl$_3$): 2.14, 2.18, 2.25, 2.29, 2.36, 2.40 (CH$_3$, each s), 3.83, 3.86, 3.97 (OCH$_3$, each s), 8.095 (aromatic H,d,J=2 Hz), 7.60 (aromatic H,dd,J$_1$=2,J$_2$=8.8 Hz), 7.05(aromatic H,d,J=8.8 Hz).

EXAMPLE 21

Bis[3-[4'-[(4"-carboxy-3"-methoxy-2",5",6"-trimethyl)phenoxycarbony]-3'-methoxy-2',5',6'-trimethyl]-phenoxycarbony-4-methoxyphenyl] Sulfone Dibenzhydryl ester of 104a (200 mg, 0.14 mmol) was dissolved in 5 ml of chloroform, and to the solution was added 120 mg (0.56 mmol) of m-chloro-benzoic acid (80%) under cooling with ice-water, and the mixture was stirred for 4.5 hours.

The reaction mixture was washed with an aqueous sodium thiosulfate solution, an aqueous saturated sodium bicarbonate, and water, successively, then dried, and the solvent was evaporated in vacuo to yield 260 mg of the crude sulfone dibenzhydryl ester. The dibenzhydryl ester of 104b (260 mg, 0.18 mmol), and 90 mg of anisole (0.83 mmol) were dissolved in 5 ml of methylene chloride, and the solution was cooled to 0° C., and then a solution of trifluoroacetic acid (210 mg, 1.8 mmol) in 1 ml of methylene chloride was added thereto with stirring. After the solution was stirred at 0° C. for 3 hours, the reaction mixture was distributed between 1N—HCl and ethyl acetate. The organic phase was washed with water, dried (Na$_2$SO$_4$), and then evaporated to dryness in vacuo, to yield 248 mg of the crude product. The product was recrystallized from ethanol (99%) to provide 123 mg of 104b. Yield: 80.9%. M.p. 294°–295° C. (dec.)

Elementary Analysis (for C$_{60}$H$_{62}$O$_{20}$S.½H$_2$O), Theory(%): C;63.04, H;5.49, S;2.81; Found (%): C;62.94, H;5.55, S;2.80; NMR (CDCl$_3$): 2.12, 2.16, 2.23, 2.27, 2.34, 2.38(CH$_3$, each s), 3.80, 3.85, 4.04(OCH$_3$, each s), 8.65(aromatic H, d, J=2.6 Hz), 8.20(aromatic H, dd, J=2.2 Hz, J=9.0 Hz), 7.20(aromatic H, d, J=9.0 Hz).

EXAMPLE 22

Bis[3-[4'-[(4"-carboxy-3"-methoxy-2",5",6"-trimethyl)phenoxycarbony]-3'-methoxy-2',5',6'-trimethyl]-phenoxycarbony-4-methoxyphenyl] Sulfoxide Dibenzhydryl ester of 104a (200mg, 0.14 mmol) was dissolved in 5 ml of methylene chloride, and to the solution was added 30 mg (0.14 mmol) of m-chloro-benzoic acid (80%) under cooling with ice-water, and the mixture was stirred at 0° C. for 4.5 hours. The reaction mixture was washed with 5% aqueous sodium thiosulfate, an aqueous saturated sodium bicarbonate, and water, successively, and dried ($Na_2SO_4$), and then the solvent was evaporated in vacuo to yield 245 mg of the crude product. The product was purified by column chromatography (40 g of $SiO_2$, eluent: ethyl acetate—n-hexane (2:1)) to yield 151 mg of 104c-dibenzhydryl ester.

The dibenzhydryl ester of 104c (146 mg, 0.1 mmol), and 50 mg of anisole were dissolved in 5 ml of methylene chloride, and then 110 mg of trifluoroacetic acid in 1 ml of methylene chloride were added thereto with stirring under cooling with ice-water. After the solution was stirred at 0° C. for five hours, the reaction mixture was evaporated to dryness in vacuo, the residue was distributed between 1N HCl and ethyl acetate. The organic phase was washed with water, dried ($Na_2SO_4$), and the solvent was evaporated in vacuo, to yield 126 mg of the crude product. The product was recrystallized from ether—n-hexane to provide 118 mg of the crude compound 104c.

Then, the compound was further recrystallized from ethanol (99%) to provide 95 mg of 104c. M.p. 193°–5° C.

Elementary Analysis (for $C_{60}H_{62}O_{19}S \cdot H_2O$), Theory: C;63.33, H;5.72, S;2.69; Found : C;63.37, H;5.67, S;2.82; NMR($CDCl_3$): 2.11, 2.16, 2.23, 2.27, 2.34, 2.38($CH_3$, each s), 3.81, 3.85, 4.01($OCH_3$, each s), 8.35(aromatic H, d, J=2.2 Hz), 7.92(aromatic H, dd, J=2.2, J'=9.0 Hz), 7.21(aromatic H, d, J=9.0 Hz).

EXAMPLE 23

Bis[3-[4'-[(4"-pivaroyloxymethyloxycarbonyl-3"-methoxy-2",5",6"-trimethyl)phenoxycarbonyl]-3'-methoxy-2',5',6'-trimethyl]-phenoxycarbonyl-4-methoxyphenyl] Sulfide A mixture containing 500 mg (0.45 mmol) of 104a, 265 mg (1.09 mmol) of pivaroyloxymethyl iodide, 216 mg (1.56 mmol) of potassium carbonate and 25 ml of acetone was stirred at room temperature for 16 hours. To the mixture was added 200 ml of ice-water, and the resultant mixuture was extracted with ethyl acetate. The organic phase was washed with water, dried ($Na_2SO_4$), and the solvent was evaporated in vacuo, to yield 0.65 g of the crude product. The product was recrystallized from ethyl acetate—n-hexane to provide 0.516 g of 104d. M.p. 120° C. (dec.)

Elementary Analysis (for $C_{72}H_{82}O_{22}S \cdot \frac{1}{2}$ hexane), Theory (%): C;65.69, H;6.73, S;2.28; Found (%): C;65.53, H;6.53, S;2.33.

EXAMPLE 24

3-Carboxy-4-methoxyphenyl{3'-[4"-[(4'''-carboxy-3'''-methoxy-2''',5''',6'''-trimethylphenoxycarbony)-3"-methoxy-2",5",6"-trimethylphenoxycarbonyl]-4-methoxyphenyl]} Sulfide

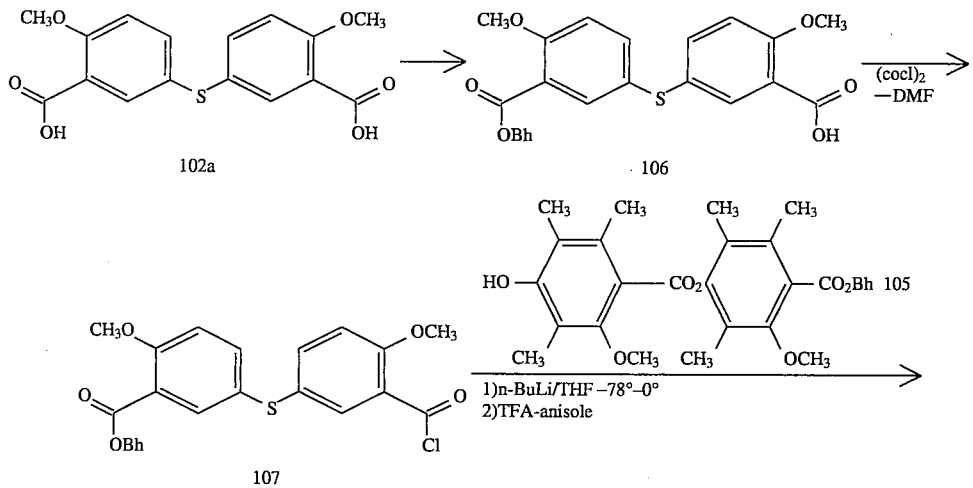

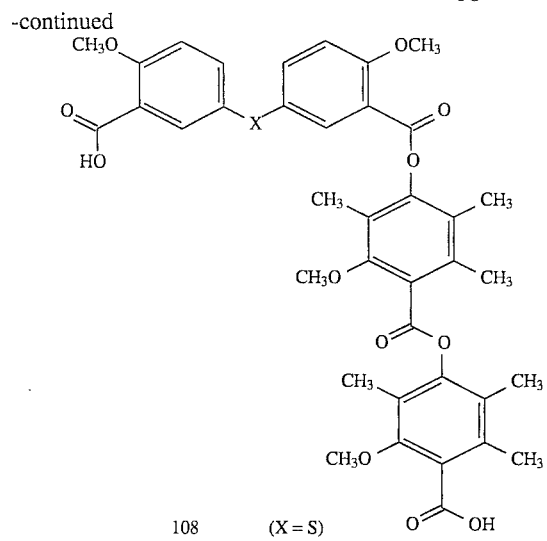

108 (X = S)

[Step 1]

Compound 102a (1.31 g, 3.9 mmol) was dissolved in 50 ml of methylene chloride, and to the solution was added 0.8 g (4.1 mmol) of diphenyldiazomethane under cooling with ice-water, and the mixture was stirred for 1.8 hours. The solvent was evaporated in vacuo, and the residue was applied to column chromatography (SiO$_2$, 150 g), and it was eluted with benzene—ethyl acetate (5:1) and then chloroform—methanol (9:1), to yield 1.06 g of 106 (54%).

[Step 2]

Compound 106 (300 mg, 0.6 mmol) and 761 mg of oxalyl chloride (0.52 mmol) were reacted by a similar procedure to that of Step 1 in Example 20, to provide 9 ml of the solution of 107 in anhydrous tetrahydrofuran. Then, 341 mg (0.6 mmol) of 105 in 15 ml of the anhydrous tetrahydrofuran, and n-butyl lithium in hexane (0.37 ml, 1.55M) were subjected to condensation reaction according to Step 2 in Example 20, to yield 688 mg of the crude product. The product was purified by silica gel chromatography (40 g of SiO$_2$, eluent: ethyl acetate—n-hexane (1:2)), to yield 213 mg (0.2 mmol) of the dibenzhydryl ester.

The dibenzhydryl ester obtained above was dissolved in 10 ml of methylene chloride, and the deprotection was conducted using 231 mg (2 mmol) of trifluoroacetic acid and 100 mg (0.92 mmol) of anisole according to the procedure of Step 2 in Example 20, to yield 123 mg of 108. M.p. 192°–194° C. (recrystallized from aqueous ethanol).

Elementary Analysis (for $C_{38}H_{38}O_{12}S$), Theory (%): C;63.40, H;5.30, S;4.36; Found (%): C;63.50, H;5.33, S;4.46; NMR (CDCl$_3$): 2.14, 2.19, 2.25, 2.29, 2.35, 2.39 (CH$_3$, each s), 3.83, 3.85, 3.97, 4.08 (OCH$_3$, each s), 8.08 (aromatic H,d,J=2.4 Hz), 8.18 (aromatic H,d,J=2.4 Hz), 7.60 (aromatic H,dd,J=2.4 Hz,J'=8.8 Hz), 7.55 (aromatic H,dd, J=2.4 Hz,J'=8.8 Hz), 7.03 (aromatic H,d,J=8.8 Hz), 7.05 (aromatic H,d,J=8.8 Hz).

EXAMPLE 25

Bis[3-(4'-carboxy-3'-methoxy-2',5',6'-trimethylphenoxycarbonyl)-4-methoxyphenyl] Sulfide (110b)

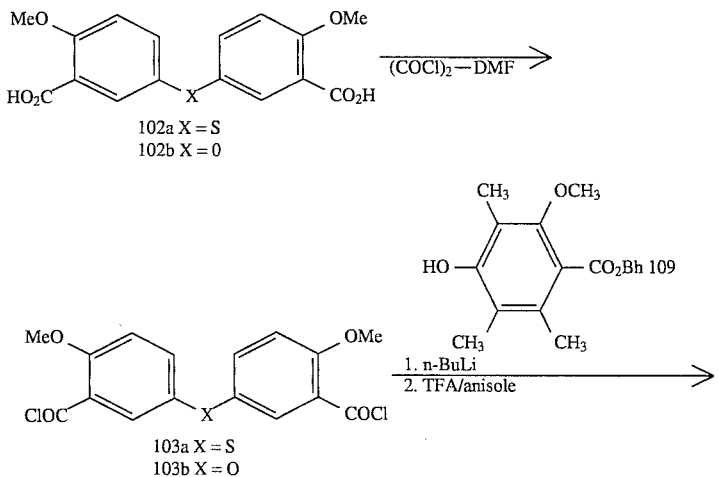

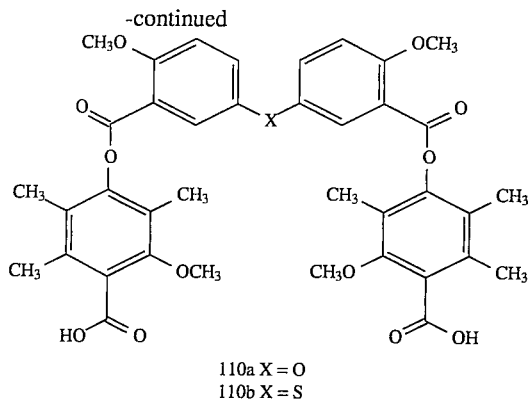

110a X = O
110b X = S

Compound 102a (150 mg, 0.45 mmol) and 0.4 ml of oxalyl chloride (4.6 mmol) were reacted in a similar procedure to that of Step 1 in Example 20, to provide 3 ml of the solution of 103a in anhydrous tetrahydrofuran. Then, 338 mg (0.9 mmol) of 109 which had been dissolved in ml of the anhydrous tetrahydrofuran, and 0.56 ml of n-butyl lithium in hexane (1.55M, 0.9 mmol) were subjected to condensation reaction according to Step 2 in Example 20, to yield 504 mg of the composition, which was purified by silica gel chromatography (35 g of $SiO_2$, eluent: ethyl acetate—n-hexane (2:3)), to yield 0.464 g of the dibenzhydryl ester of 110b.

The dibenzhydryl ester (0.464 g) obtained above was dissolved in 10 ml of methylene chloride, and the deprotection was conducted using 215 mg of anisole (2 mmol) and 503 mg of trifluoroacetic acid (4.4 mmol) according to the procedure of Step 2 in Example 20, to yield 227 mg of 110b. M.p. 237°–239° C. (recrystallized from benzene).

Elementary Analysis (for $C_{38}H_{38}O_{12}S.\frac{1}{2}$ benzene), Theory(%): C;65.06, H;5.51, S;4.11; Found (%): C;64.98, H;5.45, S;4.23; NMR($CDCl_3$): 2.08, 2.09, 2.32 ($CH_3$, each s), 3.81, 3.95 ($OCH_3$, each s), 8.09 (aromatic H,d,J=2.4 Hz), 7.60 (aromatic H,dd,J=2.4 Hz,J'=8.8 Hz), 7.03 (aromatic H,d,J=8.8 Hz).

EXAMPLE 26

Bis[3-(4'-carboxy-3'-methoxy-2',5',6'-trimethylphenoxycarbonyl)-4-methoxyphenyl] Ether (110a)

Compound 102b (150 mg, 0.47 mmol) and 0.41 ml of oxalyl chloride (47 mmol) were reacted in a similar procedure to that of Step 1 in Example 20, to provide 5 ml of the solution of 103b in anhydrous tetrahydrofuran. Then, 355 mg (0.94 mmol) of 109 which had been dissolved in 15 ml of the anhydrous tetrahydrofuran, and 0.59 ml of n-butyl lithium in hexane (1.55M, 0.94 mmol) were subjected to condensation reaction according to Step 2 in Example 20, to yield 539 mg of the composition, which was purified by silica gel chromatography (35 g of $SiO_2$, eluent: ethyl acetate—n-hexane (2:3)), to yield 490 mg of the dibenzhydryl ester of 110a.

The dibenzhydryl ester (490 mg, 0.47 mmol) obtained above was dissolved in 5 ml of methylene chloride, and the deprotection was conducted using 228 mg (2.1 mmol) of anisole and 534 mg (4.7 mmol) of trifluoroacetic acid according to the procedure of Step 2 in Example 20, to yield 214 mg of 110a. M.p. 194°–5° C. (recrystallized from aqueous ethanol).

Elementary Analysis (for $C_{38}H_{38}O_{13}.H_2O$), Theory(%): C;63.28, H;5.38; Found (%): C;63.33, H;5.59; NMR ($CDCl_3$): 2.11, 2.12, 2.33 ($CH_3$, each s), 3.82, 3.95 ($OCH_3$, each s), 7.73 (aromatic H,d,J=3 Hz), 7.27 (aromatic H,dd, J=3 Hz,J'=9.2 Hz), 7.06 (aromatic H,d,J=9.2 Hz).

EXAMPLE 27

Bis[3-[4'-[(4"-carboxy-3"-methoxy-2",5",6"-trimethylphenoxycarbonyl]-3'-methoxy-2',5',6'-trimethylphenoxycarbony]-4-methoxyphenyl] Ether (120)

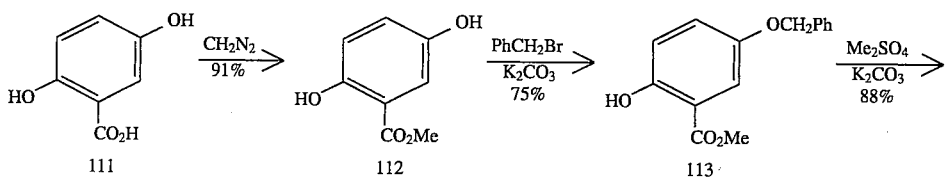

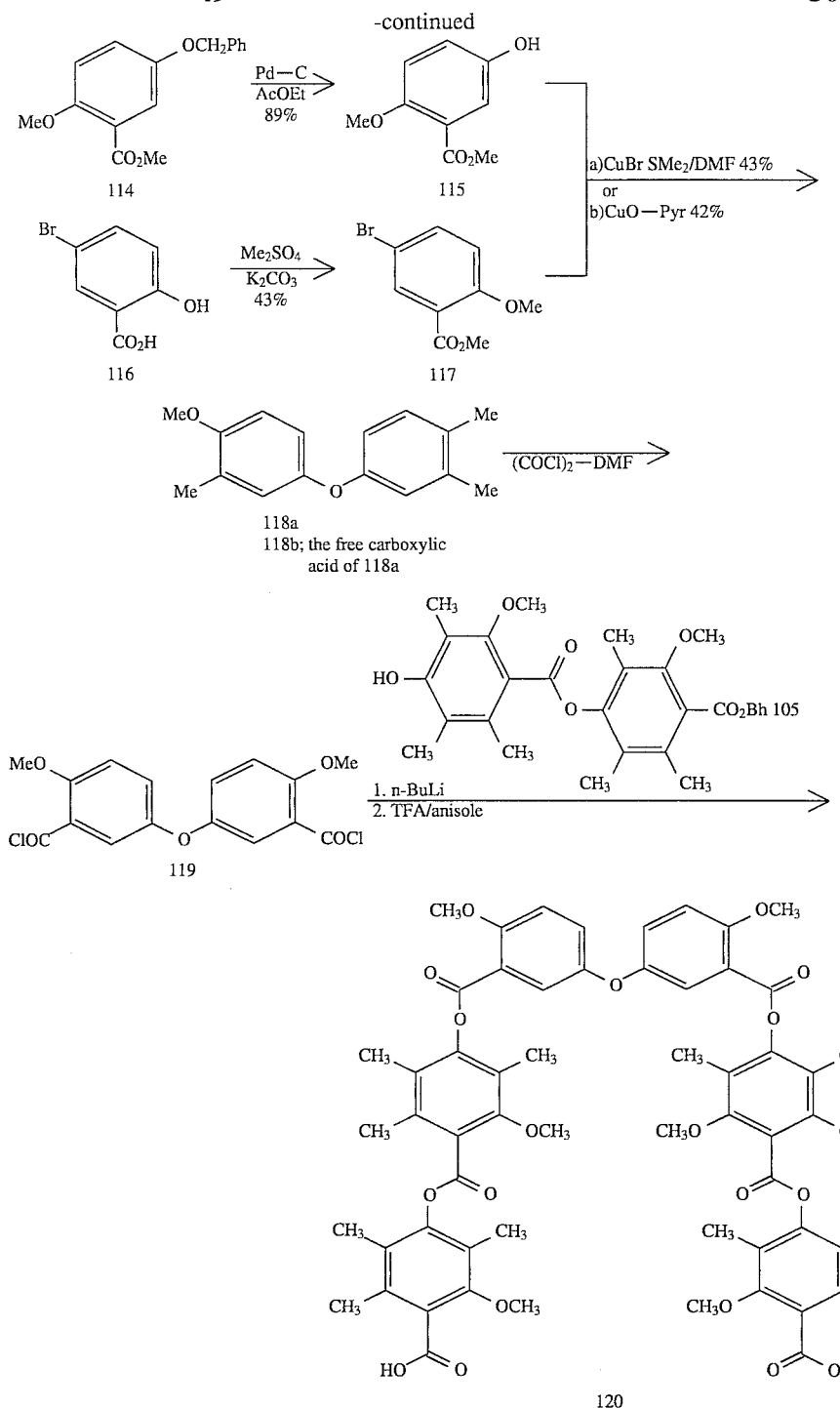

[1] Preparation of the Intermediate 118a

Compound 115 (200 mg, 1.1 mmol) was dissolved in 5 ml of DMF, and 46 mg of NaH (60% in oil) (1.15 mmol) was added thereto, and the mixture was stirred for 1.5 hours. After 690 mg (3.36 mmol) of copper bromide (I)—dimethyl sulfide complex was added to the mixture, 270 mg of the bromide 117 (1.1 mg) which had been dissolved in 0.5 ml of DMF was added thereto, and the resultant mixutre was refluxed with stirring for 22 hours. After cooling, the reaction mixture was distributed between 1N HCl and ethyl acetate, and the organic phase was washed with N—HCl, water, and the saturated brine, successively, and then dried ($Na_2SO_4$). The solvent was evaporated to dryness, and the residue (383 mg) was applied to silica gel chromatography (40 g of $SiO_2$, eluent: ethyl acetate: hexane (2:3)), to yield 163 mg of 118a. M.p. 94°–95° C. (ethyl acetate—hexane (2:3))

Elementary Analysis (for $C_{18}H_{18}O_7$), Theory (%): C;62.26, H;5.25; Found (%): C;62.42, H;5.24.

Alternatively, the compound 118a may be obtained by the following procedure.

A mixture containing 200 mg (1.1 mmol) of 115, 272 mg of 117 (1.1 mmol), 167 mg of K$_2$CO$_3$ (1.2 mmol), and 4 ml of pyridine was heated to 130° C. (oil bath) with stirring for 15 minutes, and then 87 mg of cupric oxide (II) (1.1 mmol) was added thereto, and the mixture was heating to 140° C. (oil bath) with stirring for 23 hours. After cooling, the reaction mixture was diluted with 50 ml of ether, and the resultant precipitates were filtered off, and then the filtrate was washed with the dilute hydrochloric acid, water, and the saturated brine, successively, and then dried (Na$_2$SO$_4$). The solvent was evaporated to dryness, and the residue (293 mg) was subjected to silica gel chromatography, to yield 161 mg of 118a. Yield: 42.3%.

[2] Preparation of the Intermediate 118b

Compound 118a (684 mg, 2 mmol) was dissolved in 10-ml of methanol, and 5 ml of 1M potassium hydroxide aqueous solution was added thereto, and then the mixture was heated under reflux for 5 hours. The reaction mixture was evaporated to dryness in vacuo, and the residue was distributed between 1N HCl and ethyl acetate. After the organic phase was washed with water and dried (Na$_2$SO$_4$), the solvent was evaporated to dryness, and then the residue (560 mg) was recrystallized from methanol, to yield 268 mg of 118b. M.p. 178°–180° C.

Elementary Analysis (for C$_{16}$H$_{14}$O$_7$), Theory (%): C;60.32, H;4.47; Found (%): C;60.38, H;4.43.

[3] Preparation of the Title Compound

Compound 118b (100 mg, 0.31 mmol) and 0.3 ml of oxalyl chloride (3.4 mmol) were reacted in a similar procedure to that of Step 1 in Example 20, to provide 5 ml of the solution of 119 in anhydrous tetrahydrofuran. Then, 357 mg (0.63 mmol) of 105 which had been dissolved in 10 ml of the anhydrous tetrahydrofuran, and 0.39 ml of n-butyl lithium in hexane (1.59M, 0.62 mmol) were subjected to condensation reaction according to Step 2 in Example 20, to yield 490 mg of the crude product. The compound was purified by silica gel chromatography (45 g of SiO$_2$, eluent: ethyl acetate— n-hexane (2:3)), to yield 443 mg of the dibenzhydryl ester of 120.

The dibenzhydryl ester of 120 (440 mg, 0.31 mmol) obtained above was dissolved in 5 ml of methylene chloride, and the deprotection was conducted using 150 mg (1.4 mmol) of anisole and 370 mg (3.2 mmol) of trifluoroacetic acid according to the procedure of Step 2 in Example 20, to yield 285 mg of 120.

M.p. 258°–260° C. (recrystallized from aqueous ethanol). Elementary Analysis (for C$_{60}$H$_{62}$O$_{19}$·½EtOH), Theory (%): C;65.80, H;5.75; Found (%): C;66.00, H;5.90; NMR (CDCl$_3$): 2.16, 2.20, 2.26, 2.29, 2.36, 2.38, 2.40 (CH$_3$, each s), 3.83, 3.86, 3.97 (OCH$_3$, each s), 7.74(aromatic H,d,J=3.2 Hz), 7.29(aromatic H,dd,J=3.2 Hz,J'=9.2 Hz), 7.08 (aromatic H,d,J=9.2 Hz).

EXAMPLE 28

Trans-1,2-bis[4'-(4"-carboxy-3"-methoxy-2",5",6"-trimethylphenoxycarbonyl)-3'-methoxy-2',5',6'-trimethylphenoxycarbony]Ethene (121a)

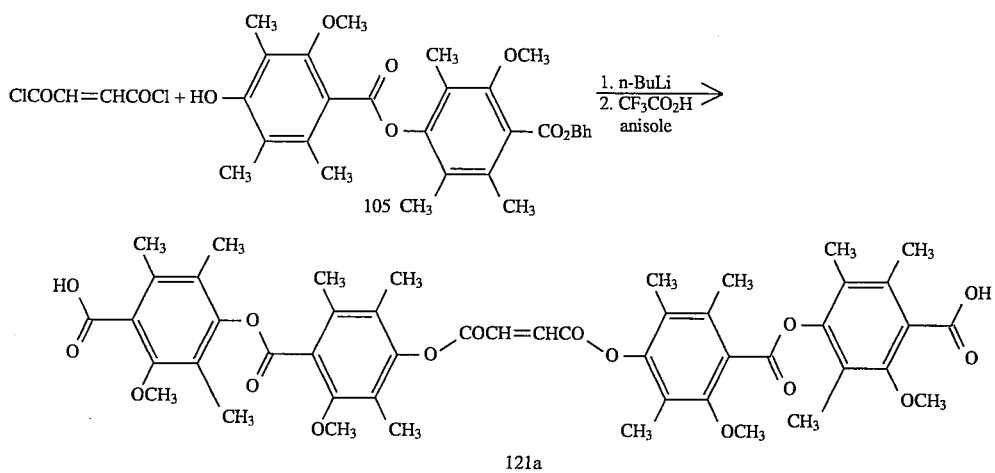

121a

Compound 105 (2.0 g, 3.5 mmol) was dissolved in ml of anhydrous tetrahydrofuran, and 2.2 ml of n-butyl lithium in hexane (1.59M) was added dropwise slowly at −78° C. The mixture was stirred at −78° C. for 50 minutes, and 270 mg of fumaryl chloride (0.19 ml, 1.77 mmol) which had been dissolved in 3 ml of tetrahydrofuran was added dropwise thereto. After the mixture was stirred at −78° C. for additional 4.5 hours, the solvent was evaporated in vacuo, and then the residue was distributed between 1N HCl and ethyl acetate. The organic phase was washed with water, dried, and then the solvent was evaporated in vacuo, to yield 2.267 g of the crude dibenzhydryl ester.

The crude product (2.0 g) obtained above was dissolved in 50 ml of methylene chloride, and 0.82 g (7.6 mmol) of anisole and 1.87 g (16.4 mmol) of trifluoroacetic acid were added thereto at 0° C. and the mixture was stirred at 0° C. for 3.5 hours. The solvent was evaporated in vacuo, and the residue was washed with ether to provide 1.24 g of 121a as a colorless solid. The compound was recrystallized from N,N-dimethylformamide. M.p. above 300° C.

Elementary Analysis (for C$_{48}$H$_{52}$O$_{16}$·½H$_2$O·½DMF) Theory (%): C;64.01, H;5.91; Found (%): C;64.01, H;6.09; NMR (d$_6$-DMSO): 2.45, 2.48, 2.52, 2.53, 2.53, 2.70 (CH$_3$, each s), 4.07, 4.11 (OCH$_3$, each s), 7.78 (aromatic H,s).

EXAMPLE 29

1,2-Bis[4'-(4"-carboxy-3"-methoxy,2",5",6"-trimethylphenoxycarbonyl)-3'-methoxy-2',5',6'-trimethylphenoxycarbony]Ethane (122)

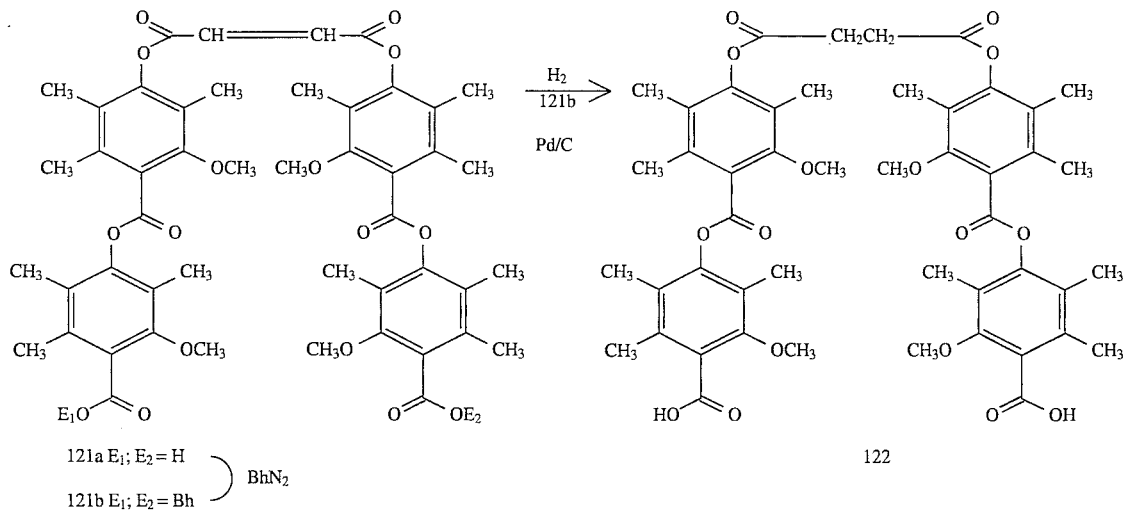

121a $E_1$; $E_2$ = H
121b $E_1$; $E_2$ = Bh
} BhN$_2$

The dibenzhydryl ester 121b (100 mg) which had been obtained in Example 28 was dissolved in the mixture consisting of 5 ml of ethyl acetate and 0.5 ml of acetic acid, and the resultant mixture was reduced at atmospheric pressure using 20 mg of 10% Pd-carbon as catalyst. The catalyst was filtered off, and the precipitated crystals were dissolved in chloroform—methanol, and the solution was combined with the above filtrate. The mixture was evaporated in vacuo, and the residue was distributed between ethyl acetate and 1N HCl, and the organic phase was washed with water, dried (Na$_2$SO$_4$), and then evaporated to dryness in vacuo to yield 92 mg of the colorless solid. The solid was recrystallized from chloroform—n-hexane to yield 42 mg of 122. M.p. >270° C. (dec.).

Elementary Analysis (for $C_{48}H_{54}O_6$), Theory (%): C;65.00, H;6.14; Found (%): C;65.17, H;6.11; NMR (d$_6$-DMSO): 2.04, 2.07, 2.17, 2.18, 2.19, 2.32 (CH$_3$, each s), 3.18 (CH$_2$,s), 3.72, 3.73 (OCH$_3$,s,6H each).

EXAMPLE 30

Thielocin B3

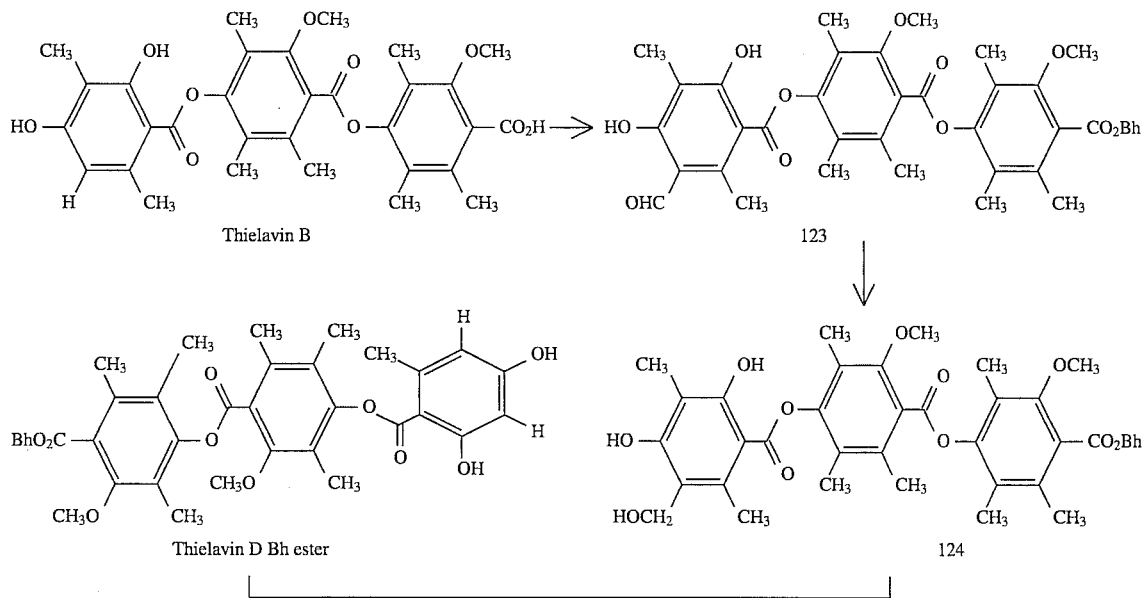

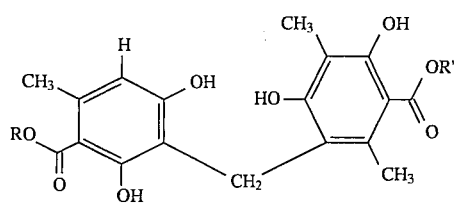
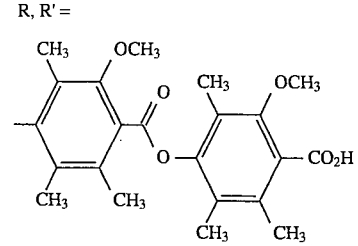

Thielocin B3

[Step 1]

Thielavin B (5.0 g, 8.82 mmol) was dissolved in 100 ml of trifluoroacetic acid, and the solution was cooled to 0° C. To the solution was added 1.5 g of hexamethylenetetramine (0.01 mmol), and the mixture was stirred at 0° C. for one hour, and then it was heated at 50° C. (bath temperature) with stirring for 4.5 hours. The reaction mixture was evaporated to dryness in vacuo, and to the residue was added 300 ml of water, and then the mixture was heated at 60° C. (bath temperature) with stirring for 6 hours. After cooling, the precipitated solid was filtered off, washed with water thoroughly, and then dissolved in about 200 ml of ethyl acetate. The solution was dried over $Na_2SO_4$, and the solvent was evaporated in vacuo to yield 5.34 g of the foam. The foam was dissolved in 100 ml of chloroform, and 1.94 g of diphenyldiazomethane was added thereto at 0° C. and the mixture was stirred for two hours The solvent was evaporated in vacuo, and the residue (5.84 g) was subjected to silica gel chromatography (350 g of $SiO_2$, eluent: ethyl acetate—n-hexane (1:4)), to yield 2.32 g of 123.

[Step 2]

Compound 123 (2.03 g, 2.67 mmol) obtained above was dissolved in 50 ml of methanol, and 0.5 g (0.013 mol) of solid $NaBH_4$ was added thereto in small portions at room temperature, and after such addition was completed, the resultant mixture was stirred for additional 1.5 hours. The reaction mixture was concentrated in vacuo, and the residue was distributed between 1N HCl and ethyl acetate. The organic phase was washed with a saturated brine, dried ($Na_2SO_4$), and then evaporated in vacuo to yield 2.22 g of the crude product. The product was recrystallized from the mixture consisting of ethyl acetate and n-hexane (1:3) to yield 1.75 g of 124.

NMR ($CDCl_3$): 2.09, 2.12, 2.17, 2.21, 2.25, 2.40, 2.65 ($CH_3$, each s), 3.57, 3.83 ($OCH_3$, each s), 5.03 ($CH_2OH$, br.S), 8.50 (s,OH), 11.65 (s,OH).

[Step 3]

Compound 124 (1.5 g, 2 mmol), and the benzhydry ester of thielavin D (1.4 g, 2 mmol) were dissolved in 150 ml of toluene, and 0.24 ml (2 mmol) of boron trifluoride diethyl ether complex was added thereto, and the mixture was stirred at room temperature for 30 minutes. The reaction mixture was diluted with 150 ml of ethyl acetate, washed with water, and then dried ($Na_2SO_4$). The mixture was evaporated in vacuo, and the residue (3.61 g) was dissolved in 40 ml of methylene chloride, and to the solution were added 0.96 g of anisole and 2.2 g of trifluoroacetic acid under cooling with ice-water, and the mixture was stirred for one hour. The resultant mixture was left standing overnight, and then the solvent was evaporated in vacuo. To the residue was added the dilute hydrochloric acid, and the precipitating oil was collected by decantation, and it was dissolved in ethyl acetate. The ethyl acetate phase was washed with water, dried ($Na_2SO_4$), and evaporated in vasuo to yield 3.79 g of the crude product. The product was purified by silica gel chromatography (eluent: chloroform—methanol—acetic acid=500:50:25), to yield 1.234 g of the thielocin B3.

Thielocin B3: recrystallized from an aqueous ethanol, m.p. 205°–207° C. (dec.)

IR (KBr): 3400, 1740, 1710, 1648, 1610, 1280, 1145 $cm^{-1}$, NMR ($CDCl_3$): 2.13, 2.18, 2.26, 2.29, 2.35, 2.41, 2.65, 2.89 ($CH_3$, each s), 3.85, 3.86 ($OCH_3$, each s), 6.37(aromatic H,s.), 11.52, 12.52 each s, disappeared by adding $D_2O$); Elementary Analysis (for $C_{62}H_{66}O_{20} \cdot 2H_2O$), Theory (%): C;64.03, H;6.22; Found (%): C;63.80, H;6.05.

EXAMPLE 31

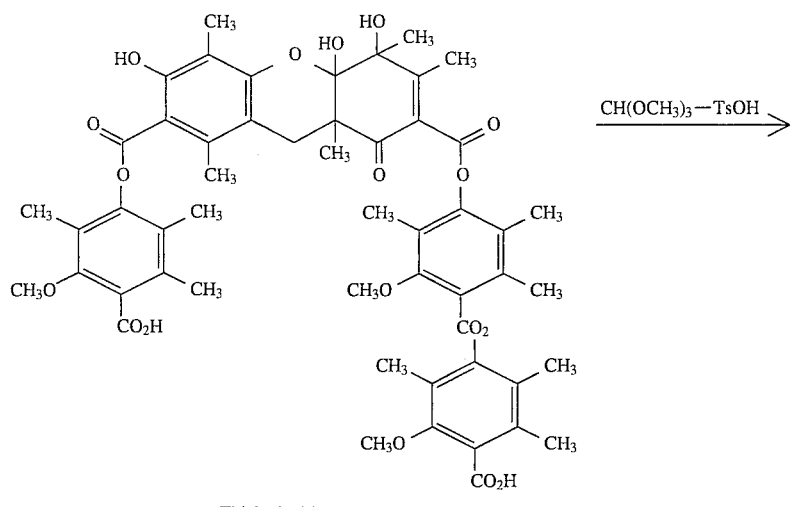

Thielocin A1

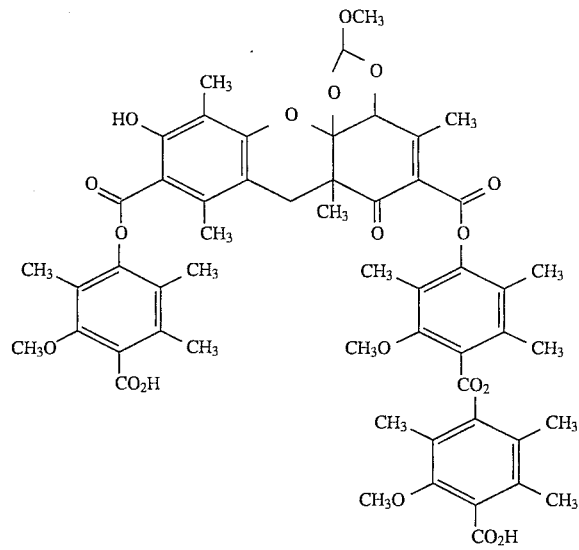

125

To a solution of thielocin A1 (6.5 mg) in 0.3 ml of chloroform were added trimethyl ortho-formate (1.8 ml) and p-toluene sulfonic acid (60 mg), and the mixture was left standing at room temperature for five days. The reaction mixture was distributed between ethyl acetate and water, and the organic phase was dried ($Na_2SO_4$), and evaporated in vacuo. The residue was purified by thin layer chromatography (Developer: $CHCl_3$:MeOH:water 62:25:4, Rf: 0.3) to yield 5.3 mg of 125. M.p. 198°–200° C. HRMS MNa$^+$ bbsd m/z 1061. 3763 (Theory: 1061.3779 for $C_{56}H_{62}O_{19}$)

EFFECT OF THE INVENTION

The compounds of the present invention were tested for their Phospholipase $A_2$ inhibitory activity by the following procedure.

Method

1-Palmitoyl-2-[1-$^{14}$C]-linoleoyl L-3-Phosphatidylethanolamine (Amersham, Inc., 59 mCi/mmol) were diluted with L-α-phosphatidylethanolamine (Sigma, Co., from egg albumin) [2,000 dpm/nmol], and the dilution was sonicated. The resultant dilution was used as a substrate. The $PLA_2$ (phospholipase $A_2$) which was used in the test was from rat platlets. The $PLA_2$ and the substrate preparation were added to a solution of $CaCl_2$ (3 mM) in Tris-buffer (0.1M, pH 7.4), and the mixture was allowed to react at 37° C. for 20 minutes. Then, the reaction was terminated by adding 1.25 ml of Dole's reagent to the reaction mixture and stirring immediately the resultant mixture. To the mixture was added 0.5 ml of distilled water and 0.8 ml of n-heptane, and the mixture was stirred, centrifuged, and the supernatant was taken into another tube. To this supernatant were added additional 0.8 ml of n-heptane and silica gel, and the mixture was stirred, centrifuged, and the supernatant was taken into vials. Toluene cocktail was added to the vials. The amount of free fatty acid released by $PLA_2$ was determined using liquid scintillation counter.

Inhibitory activity (%) was estimated by the formula: [(DPM value at the addition of the inhibitor–DPM value without $PLA_2$)/(DPM value with only $PLA_2$–DPM value without $PLA_2$)]×100.

Results

The results are shown in the following Table 1.

TABLE 1

| PLA$_2$ inhibitory activity [IC50 (µM)] | |
|---|---|
| Compound No. | Rat platelets |
| 8 | >330 |
| 9 | >480 |
| 52 | 0.16 |
| 50 | 4.6 |
| 44 | 0.13 |
| 48 | 3.0 |
| 54 | 0.88 |
| 59 | 1.45 |
| 56 | 0.035 |
| 62 | 0.95 |
| 74 | 0.070 |
| 77 | 0.34 |
| 104a | 0.049 |
| 108 | 2.1 |
| 104b | 0.050 |
| 121 | 0.33 |
| 120 | 0.042 |
| 110b | 2.5 |
| 104c | 0.12 |
| 110a | 3.4 |
| 122 | 0.04 |

We claim:

1. A thielocin derivative of the formula:

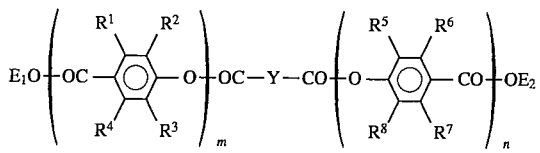

wherein $R^1$, $R^2$, $R^3$, $R^4$, $R^5$, $R^6$, $R^7$, and $R^8$ are independently hydrogen, lower alkyl, lower alkoxy, hydroxy, or halogen;

$E_1$ and $E_2$ are independently hydrogen; unsubstituted $C_1$–$C_8$ alkyl, methoxymethyl, ethoxymethyl, iodoethyl, ethoxyethyl, methylthioethyl, methanesulfonylethyl, or trichloroethyl; unsubstituted $C_3$–$C_8$ alkenyl, or phenylpropenyl; unsubstituted $C_7$–$C_{19}$ aralkyl, methylbenzyl, dimethylbenzyl, methoxybenzyl, ethoxybenzyl, nitrobenzyl, aminobenzyl, diphenylmethyl, trityl, di-t-butylhydroxybenzyl, phthalidyl, or phenacyl; unsubstituted $C_6$–$C_{12}$ aryl, tolyl, diisopropylphenyl, xylyl, trichlorophenyl, pentachlorophenyl, or indanyl; noncyclic straight or branched $C_2$–$C_{15}$ alkanoyloxyalkyl, cyclohexanacetoxyethyl, or cyclohexanecarbonyloxycyclohexylmethyl;

m and n are independently an integer of 0 to 4, provided that m and n are not simultaneously 0;

—Y— is a bivalent group of the following structure:

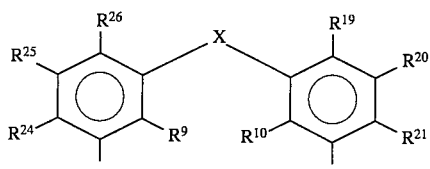

wherein

X is a single bond, CH$_2$, O, S, SO, or SO$_2$;

$R^{9'}$ and $R^{10'}$ are independently hydrogen, lower alkyl, lower alkoxy, hydroxy, or halogen;

$R^{19}$, $R^{20}$, $R^{21}$, $R^{24}$, $R^{25}$, and $R^{26}$ are independently hydrogen, lower alkyl, lower alkoxy, hydroxy, or halogen, or a pharmaceutically acceptable salt thereof.

2. A thielocin derivative of the formula:

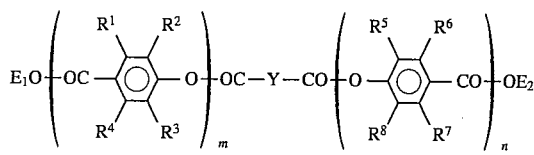

wherein $R^1$, $R^2$, $R^3$, $R^4$, $R^5$, $R^6$, $R^7$, and $R^8$ are independently hydrogen, lower alkyl, lower alkoxy, hydroxy, or halogen, $E_1$ and $E_2$ are independently hydrogen; unsubstituted $C_1$–$C_8$ alkyl, methoxymethyl, ethoxymethyl, iodoethyl, ethoxyethyl, methylthioethyl, methanesulfonylethyl, or trichloroethyl; unsubstituted $C_3$–$C_8$ alkenyl, or phenylpropenyl; unsubstituted $C_7$–$C_{19}$ aralkyl, methylbenzyl, dimethylbenzyl, methoxybenzyl, ethoxybenzyl, nitrobenzyl, aminobenzyl, diphenylmethyl, trityl, di-t-butylhydroxybenzyl, phthalidyl, or phenacyl; unsubstituted $C_6$–$C_{12}$ aryl, tolyl, diisopropylphenyl, xylyl, trichlorophenyl, pentachlorophenyl, or indanyl; noncyclic straight or branched $C_2$–$C_{15}$ alkanoyloxyalkyl, cyclohexanacetoxyethyl, or cyclohexanecarbonyloxycyclohexylmethyl;

m and n are independently an integer of 0 to 3, provided that m and n are not simultaneously 0;

—Y— is a bivalent group of the following structure:

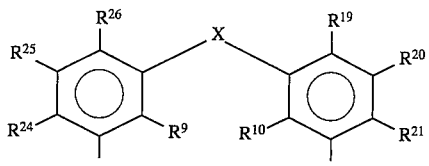

wherein

X is CH$_2$, O, S, SO, or SO$_2$;

$R^{9'}$ and $R^{10'}$ are independently hydrogen, lower alkyl, lower alkoxy, hydroxy, or halogen;

$R^{19}$, $R^{20}$, $R^{21}$, $R^{24}$, $R^{25}$, and $R^{26}$ are independently hydrogen, lower alkyl, lower alkoxy, hydroxy, or halogen, or a pharmaceutically acceptable salt thereof.

3. A thielocin derivative according to claim 1 wherein, $R^1$, $R^2$, $R^3$, $R^4$, $R^5$, $R^6$, $R^7$, and $R^8$ are independently hydrogen, lower alkyl, lower alkoxy, hydroxy, or halogen.

4. The compound [5-[4'-[4''-(4'''-Carboxy-3'''-methoxy-2''',5''',6'''-trimethylphenoxycarbony)-3''-methoxy-2'',5'',6''-trimethylphenoxycarbony]-3'-hydroxy-2',5'-dimethylphenoxycarbony]-2,4-dimethoxy-3,6-dimethylphenyl] [4''''-(2'''''-amino-2'''''-carboxyethyl)phenyl] ether or a pharmaceutically acceptable salt thereof.

* * * * *